(12) United States Patent
Stevens et al.

(10) Patent No.: US 12,274,475 B2
(45) Date of Patent: Apr. 15, 2025

(54) AUTOMATED COUPLED TORSIONAL FIXATORS AND METHOD OF USE

(71) Applicants: Peter M. Stevens, Salt Lake City, UT (US); John Colin Stevens, Salt Lake City, UT (US)

(72) Inventors: Peter M. Stevens, Salt Lake City, UT (US); John Colin Stevens, Salt Lake City, UT (US)

(*) Notice: Subject to any disclaimer, the term of this patent is extended or adjusted under 35 U.S.C. 154(b) by 0 days.

(21) Appl. No.: 18/731,261

(22) Filed: Jun. 1, 2024

(65) Prior Publication Data

US 2024/0315732 A1 Sep. 26, 2024

Related U.S. Application Data

(60) Continuation-in-part of application No. 17/670,486, filed on Feb. 13, 2022, now Pat. No. 11,998,241, which is a division of application No. 16/588,181, filed on Sep. 30, 2019, now Pat. No. 11,272,957.

(60) Provisional application No. 63/604,871, filed on Nov. 30, 2023, provisional application No. 62/741,036, filed on Oct. 4, 2018.

(51) Int. Cl.
*A61B 17/62* (2006.01)
*A61B 17/64* (2006.01)

(52) U.S. Cl.
CPC .......... *A61B 17/62* (2013.01); *A61B 17/6416* (2013.01); *A61M 2210/02* (2013.01)

(58) Field of Classification Search
CPC . A61B 17/62; A61B 17/6416; A61M 2210/02
See application file for complete search history.

(56) References Cited

U.S. PATENT DOCUMENTS

| | | | |
|---|---|---|---|
| 2,055,024 | A | 9/1936 | Bittner, Jr. |
| 4,033,340 | A | 7/1977 | Kalnberz |
| 4,365,624 | A | 12/1982 | Jaquet |
| 4,768,524 | A | 9/1988 | Hardy |
| 4,947,835 | A | 8/1990 | Hepburn et al. |
| 5,074,866 | A | 12/1991 | Sherman et al. |

(Continued)

FOREIGN PATENT DOCUMENTS

| CN | 104161578 A | 11/2014 |
|---|---|---|
| DE | 3305597 A1 | 8/1984 |

(Continued)

*Primary Examiner* — Nicholas J Plionis
(74) *Attorney, Agent, or Firm* — David Meibos; Maywood IP Law

(57) ABSTRACT

A system for external rotational deformity correction of an intact bone may include: a first frame member and a second frame member rotatably coupled therewith, a first bone fixation member coupled to the first frame member and to a distal segment of the intact bone, a second bone fixation member coupled to the second frame member and to a proximal segment of the intact bone at a first angle, an automated control mechanism coupled to the first and second frame members, and a power source for the automated control mechanism. The automated control mechanism may: receive power from the power source, rotate the first frame member to a desired relative rotational position, and position the first bone fixation member at a desired second angle to exert torsional force on the intact bone and externally reduce rotational deformity of the intact bone.

14 Claims, 26 Drawing Sheets

(56) References Cited

U.S. PATENT DOCUMENTS

| | | |
|---|---|---|
| 5,087,258 A | 2/1992 | Schewior |
| 5,358,504 A | 10/1994 | Paley et al. |
| 5,397,322 A | 3/1995 | Campopiano |
| 5,630,814 A | 5/1997 | Ross, Jr. et al. |
| 5,728,095 A | 3/1998 | Taylor et al. |
| 5,971,984 A | 10/1999 | Taylor et al. |
| 5,997,537 A | 12/1999 | Walulik |
| 6,017,341 A | 1/2000 | Windhagen et al. |
| 6,030,386 A | 2/2000 | Taylor et al. |
| 6,102,911 A | 8/2000 | Faccioli et al. |
| 6,860,883 B2 | 3/2005 | Janowski et al. |
| 7,226,449 B2 | 6/2007 | Venturini et al. |
| 7,361,176 B2 | 4/2008 | Cooper et al. |
| 8,202,273 B2 | 6/2012 | Karidis |
| 8,430,878 B2 | 4/2013 | Vasta et al. |
| 8,491,599 B2 | 7/2013 | Heilala et al. |
| 8,679,117 B2 | 3/2014 | Knuchel et al. |
| 8,814,866 B2 | 8/2014 | Vaidya |
| 8,864,763 B2 | 10/2014 | Murray et al. |
| 8,951,252 B2 | 2/2015 | Steiner et al. |
| 9,011,438 B2 | 4/2015 | Steiner et al. |
| 9,023,045 B2 | 5/2015 | Lehmann et al. |
| 9,044,271 B2 | 6/2015 | Edelhauser et al. |
| 9,101,398 B2 | 8/2015 | Singh et al. |
| 9,289,238 B2 | 3/2016 | Ross et al. |
| 9,308,025 B2 | 4/2016 | Zgonis et al. |
| 9,445,841 B2 | 9/2016 | Samchukov et al. |
| 9,757,153 B2 | 9/2017 | Jay et al. |
| 9,808,288 B2 | 11/2017 | Wong et al. |
| 10,076,375 B1 | 9/2018 | Martel |
| 11,272,957 B2 | 3/2022 | Stevens |
| 11,998,241 B2 | 6/2024 | Stevens |
| 2003/0106230 A1 | 6/2003 | Hennessey |
| 2003/0153910 A1 | 8/2003 | Janowski et al. |
| 2005/0043730 A1 | 2/2005 | Janowski et al. |
| 2006/0184169 A1 | 8/2006 | Stevens |
| 2007/0055233 A1* | 3/2007 | Brinker .............. A61B 17/62 606/54 |
| 2008/0269741 A1 | 10/2008 | Karidis |
| 2009/0036890 A1 | 2/2009 | Karidis |
| 2009/0264884 A1 | 10/2009 | Masse et al. |
| 2009/0287212 A1* | 11/2009 | Hirata .............. A61B 17/645 606/59 |
| 2010/0191239 A1 | 7/2010 | Sakkers et al. |
| 2011/0118738 A1 | 5/2011 | Vasta et al. |
| 2011/0313419 A1 | 12/2011 | Mullaney |
| 2012/0303029 A1 | 11/2012 | Vasta et al. |
| 2015/0216565 A1 | 8/2015 | Paley et al. |
| 2015/0257803 A1 | 9/2015 | Sampath et al. |
| 2016/0022314 A1 | 1/2016 | Bordeaux et al. |
| 2016/0066956 A1 | 3/2016 | Siemer et al. |
| 2017/0354439 A1 | 12/2017 | Mannanal et al. |
| 2018/0042651 A1 | 2/2018 | Little et al. |
| 2020/0275953 A1* | 9/2020 | Park .............. A61B 17/66 |

FOREIGN PATENT DOCUMENTS

| | | |
|---|---|---|
| DE | 4113083 A1 | 10/1992 |
| DE | 102015121357 A1 | 6/2017 |
| EP | 1239784 B1 | 4/2006 |
| EP | 3127498 B1 | 7/2020 |
| KR | 1015016350000 | 3/2015 |
| WO | WO 01/22892 A1 | 4/2001 |
| WO | WO2007075114 | 7/2007 |
| WO | WO2017083033 A1 | 5/2017 |
| WO | WO2017139517 A1 | 8/2017 |
| WO | WO2020178343 A1 | 9/2020 |

* cited by examiner

AUTOMATED COUPLED TORSIONAL FIXATORS AND METHOD OF USE

CROSS-REFERENCE TO RELATED APPLICATIONS

This application is a continuation-in-part of U.S. patent application Ser. No. 17/670,486 filed on Feb. 13, 2022, entitled COUPLED TORSIONAL FIXATOR AND METHOD OF USE, which is a divisional of U.S. patent application Ser. No. 16/588,181 filed on Sep. 30, 2019, entitled COUPLED TORSIONAL FIXATOR AND METHOD OF USE, which issued on Mar. 15, 2022 as U.S. Pat. No. 11,272,957, which claims the benefit of U.S. Provisional Patent Application Ser. No. 62/741,036 filed on Oct. 4, 2018, entitled COUPLED TORSIONAL FIXATOR AND METHOD OF USE. This application claims the benefit of U.S. Provisional Patent Application Ser. No. 63/604,871 filed on Nov. 30, 2023, entitled "COUPLED TORSIONAL FIXATOR AND METHOD OF USE". The foregoing are incorporated by reference as though set forth herein in their entirety.

TECHNICAL FIELD

The present disclosure relates to medical devices, systems, and methods. More specifically, the present disclosure relates to automated devices, systems, and methods for external anteversion/retroversion correction of intact bones.

BACKGROUND

In normal human development, the femur is characterized by about 11° of forward inclination of the upper femur (e.g., the neck and head of the femur) relative to the lower end of the femur (e.g., the shaft and femoral condyles). FIG. 1A illustrates an inferior view of a femur with normal anatomy, enabling proper gait with the foot facing forward.

In contrast to normal femoral development, femoral anteversion is characterized by excessive forward inclination of the upper femur relative to the lower femur, as illustrated in FIG. 1B, which illustrates a femur with 30 degrees of anteversion. Femoral anteversion results in a knee that twists inward relative to the hip, which results in "in-toeing" of the foot. This may predispose a patient to hip injuries (e.g., labrum injuries, etc.) and knee injuries (e.g., patellar injuries, ACL injuries, etc.). Persistent torsional deformity due to anteversion cannot be corrected with a brace or with physical therapy. Retroversion is the opposite deformity (backward inclination of the upper femur relative to the lower femur) and can likewise lead to injury. Anteversion and retroversion may be referred to as rotational deformities.

One remedy for anteversion/retroversion includes performing a rotational osteotomy of the femur. This typically requires internal fixation with a large plate or intramedullary rod that is usually removed once the bone has healed after the procedure. During a traditional correction procedure for femoral anteversion/retroversion, called a femoral derotation osteotomy, the surgeon cuts the femur, rotates the ball of the femur in the hip socket to a normal position, and then reattaches the resected bone portions together. A large plate or intramedullary rod is then implanted to hold the resected bone portions in a corrected orientation. However, this surgery is extremely invasive and associated with many negative features and risks. Some of the negative items associated with this procedure include: (1) significant surgical scarring; (2) over/under-correction of the anteversion/retroversion; (3) significant pain; (4) delayed walking after the procedure; (5) possible loss of fixation; (6) delayed healing; (7) non-union of the bone; (8) time/costs associated with inpatient procedures, etc.

Accordingly, devices, systems, and methods that can alleviate some, or all, of these negative features in an automated fashion with improved safety, morbidity, efficacy, compliance, healing/rehabilitation/treatment times, and/or costs, would be desirable.

SUMMARY

The automated external anteversion/retroversion correction devices, systems, and methods of the present disclosure have been developed in response to the present state of the art, and in particular, in response to the problems and needs in the art that have not yet been fully solved by currently available anteversion/retroversion correction devices, systems, and methods. In some embodiments, the automated external anteversion/retroversion correction devices, systems, and methods of the present disclosure may provide improved devices, systems, and methods for correcting anteversion or retroversion in an automated fashion that improves safety, efficacy, compliance, healing times, and/or costs for patients needing anteversion correction of an intact bone such as a femur, tibia, or other long bone. In the case of a tibia, the devices, systems, and methods disclosed herein may be used to correct inward tibial torsion or outward tibial torsion.

In some embodiments, a system for rotational deformity correction of an intact bone may include: a first frame member, a second frame member rotatably coupled to the first frame member, a first bone fixation member coupled to the first frame member and extending therefrom to couple with a distal segment of the intact bone, a second bone fixation member coupled to the second frame member and extending therefrom to couple with a proximal segment of the intact bone at a first initial angle relative to the first bone fixation member, an automated control mechanism coupled to the first frame member and the second frame member, and a power source configured to provide power to the automated control mechanism. The automated control mechanism may be configured to: receive power from the power source, rotate the first frame member to a desired relative rotational position with respect to the second frame member, and position the first bone fixation member at a desired second angle relative to the second bone fixation member to exert torsional force on the intact bone between the distal segment and the proximal segment, and externally reduce rotational deformity of the intact bone.

In some embodiments, the power source may include at least one of: a pressurized material, a mechanical spring, and a battery.

In some embodiments, the automated control mechanism may be configured to apply a continuous torsional force on the intact bone between the distal segment and the proximal segment.

In some embodiments, the automated control mechanism may be configured to apply one or more discrete torsional forces on the intact bone between the distal segment and the proximal segment.

In some embodiments, the automated control mechanism may include a stepper motor, and power source may include a battery in electronic communication with the stepper motor.

In some embodiments, the stepper motor may be controlled by a processor programmed to control at least one rotational step movement of the stepper motor over at least one period of time.

In some embodiments, the processor may be programmed to control the rotational step movement of the stepper motor to apply a plurality of discrete torsional forces on the intact bone between the distal segment and the proximal segment over the at least one period of time.

In some embodiments, a system for external rotational deformity correction of an intact bone may include: a first frame member, a second frame member rotatably coupled to the first frame member, a first bone fixation member coupled to the first frame member and extending therefrom to couple with a distal segment of the intact bone, a second bone fixation member coupled to the second frame member and extending therefrom to couple with a proximal segment of the intact bone at a first initial angle relative to the first bone fixation member, and a stepper motor coupled to the first frame member and the second frame member. The stepper motor may be configured to: receive power from an electronic power source, rotate the first frame member to a desired relative rotational position with respect to the second frame member via the power received from the electronic power source, and position the first bone fixation member at a desired second angle relative to the second bone fixation member to exert torsional force on the intact bone between the distal segment and the proximal segment, and externally reduce rotational deformity of the intact bone.

In some embodiments, the stepper motor may include a threaded drive shaft couplable with at least one of the first frame member and the second frame member. The threaded drive shaft may be configured to rotate the first frame member to the desired relative rotational position with respect to the second frame member.

In some embodiments, the threaded drive shaft may be configured to couple with the at least one of the first frame member and the second frame member via a fixation member positioned intermediate the threaded drive shaft and the at least one of the first frame member and the second frame member.

In some embodiments, the electronic power source may include a battery in electronic communication with the stepper motor.

In some embodiments, the stepper motor may be configured to apply and maintain one or more discrete torsional forces on the intact bone between the distal segment and the proximal segment.

In some embodiments, the stepper motor may be controlled by a processor programmed to control at least one rotational step movement of the stepper motor over at least one period of time.

In some embodiments, the processor may be programmed to control the rotational step movement of the stepper motor to apply a plurality of discrete torsional forces on the intact bone between the distal segment and the proximal segment over the at least one period of time.

In some embodiments, a method for external rotational deformity correction of an intact bone can utilize a device that may include: a first frame member and a second frame member rotatably coupled together, a first bone fixation member coupled to the first frame member, a second bone fixation member coupled to the second frame member, and an automated control mechanism coupled to the first frame member and the second frame member. The steps of method may include percutaneously securing the first bone fixation member to a distal segment of the intact bone, percutaneously securing the second bone fixation member to a proximal segment of the intact bone at a first initial angle relative to the first bone fixation member, and activating the automated control mechanism to correct rotational deformity of the intact bone via automation by: receiving power from a power source in communication with the automated control mechanism, rotating the first frame member to a desired relative rotational position with respect to the second frame member via the power received from the power source, moving the second bone fixation member to a second desired angle relative to the first bone fixation member, and applying a torsional force between the distal segment and the proximal segment to reduce rotational deformity of the intact bone.

In some embodiments of the method, the power source may include at least one of: a pressurized material, a mechanical spring, and a battery.

In some embodiments of the method, the automated control mechanism may be configured to apply a continuous torsional force on the intact bone between the distal segment and the proximal segment.

In some embodiments of the method, the automated control mechanism may be configured to apply one or more discrete torsional forces on the intact bone between the distal segment and the proximal segment.

In some embodiments of the method, the automated control mechanism may include a stepper motor, and the power source may include a battery in electronic communication with the stepper motor.

In some embodiments of the method, the stepper motor may be controlled by a processor programmed to control at least one rotational step movement of the stepper motor over at least one period of time.

These and other features and advantages of the present disclosure will become more fully apparent from the following description and appended claims or may be learned by the practice of the automated external rotational deformity correction devices, systems, and methods, also referred to as "anteversion/retroversion correction devices," systems, and methods, as set forth hereinafter.

BRIEF DESCRIPTION OF THE DRAWINGS

Exemplary embodiments of the present disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
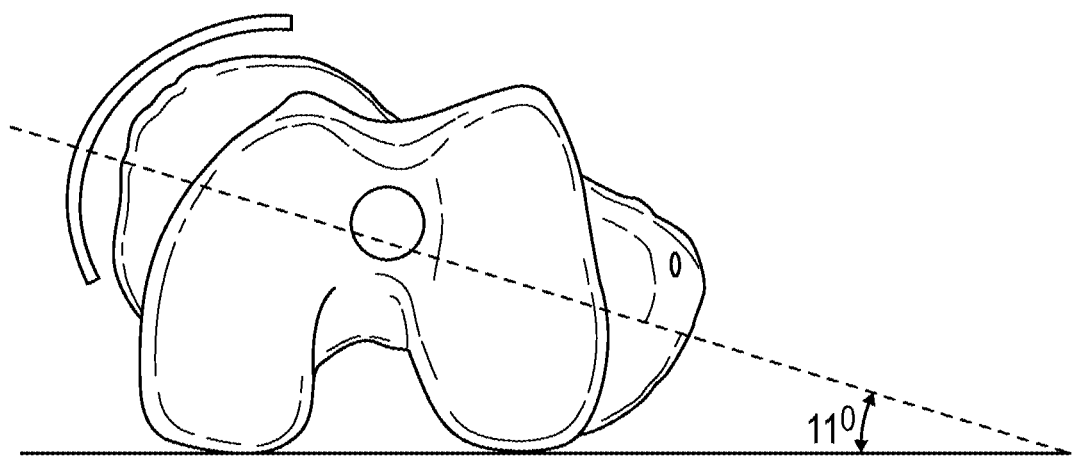
FIG. 1A is an inferior view of a normal femur.
Figure 1B:
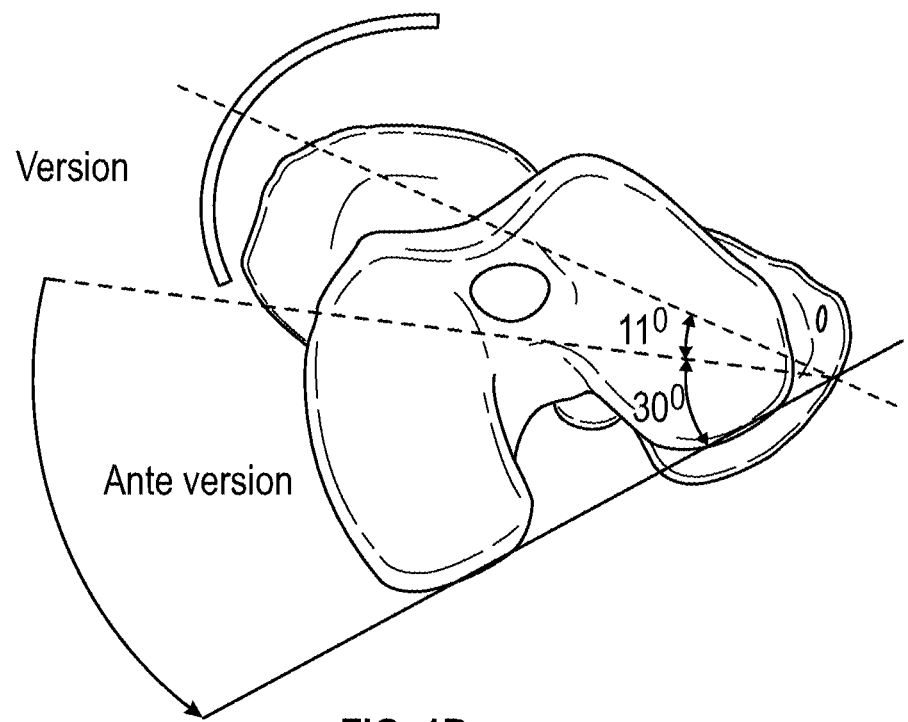
FIG. 1B is an inferior view of a femur with 30 degrees of anteversion.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms may also be applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. *Varus* means outboard deviation of the knees (away from the sagittal plane) from the line between the hip and ankle, resulting in a "bowlegged" stance. Valgus means inboard deviation of the knees (toward the sagittal plane) from the lien between the hip and ankle, resulting in a "knock-kneed" appearance.

Disclosed herein are devices and methods for anteversion/retroversion correction which are less invasive and can provide quicker/more reliable correction of torsional deformities than traditional correction procedures. Advantages of using the coupled torsional fixators disclosed herein over femoral derotation osteotomies may include: (1) ease of removal (e.g., removal of an external frame vs. removal of an internal plate or IM rod); (2) outpatient procedure vs. inpatient procedure; (3) minimal scarring (e.g., at the pin sites); (4) adjustability; (5) reduced pain; (6) immediate ability to walk following the procedure; (7) secure fixation; and (8) no bone healing is required. Full weight bearing is possible following the correction procedures disclosed herein, since the bone remains intact.

Although the present disclosure illustrates rotational deformity correction with reference to femoral bones, it will also be understood that the devices, systems, and methods disclosed herein may also be utilized to "untwist" any long bone without the need for an osteotomy to correct abnormal torsional alignment, as long as the long bone is still growing. For example, the devices, systems, and methods disclosed herein may be utilized to untwist an upper tibia in patients with inward or outward tibial torsion, etc. Deformity correction (e.g., "untwisting") may be considered to occur in the growth plate ("physis"), rather than on either side of an osteotomy. Thus, deformity correction may occur in the physis to correct angulation of a bone shaft relative to the epiphysis of the bone.

FIGS. 2-5 illustrate a coupled torsional fixator 100, as one non-limiting example of an anteversion/retroversion correction device of the present disclosure for external femoral anteversion/retroversion correction of an intact bone. The coupled torsional fixator 100 may generally include a coupled ring assembly 102, a control mechanism or turnbuckle assembly 104, a first fixation pin assembly 106, and a second fixation pin assembly 108.

In use, the first and second fixation pin assemblies 106, 108 may be percutaneously affixed to a patient's intact bone, such as an intact femur comprising a distal femoral segment and a proximal femoral segment on opposing sides of a physis or physeal growth plate of the intact femur. The turnbuckle assembly 104 may then be adjusted to provide and maintain a corrective torsional force between the first and second fixation pin assemblies 106, 108. The amount of corrective torsional force between the first and second fixation pin assemblies 106, 108 can be gradually adjusted until a partial or complete anteversion/retroversion correction has been achieved.

As shown in FIGS. 2-6B, the coupled ring assembly 102 may include a first frame member, first arcuate segment, or outer ring assembly 103 comprising a first outer ring element 120 and a second outer ring element 122 configured to couple with each other, as well as a second frame member, second arcuate segment, or inner ring element 124 which may be concentrically nested between the first and second outer ring elements 120, 122 and may rotatably couple with the first and second outer ring elements 120, 122. A ring assembly bore 126 may be defined by the inner surface of inner ring element 124. A fixator central axis 101 may extend through the center of ring assembly bore 126.

In at least one embodiment, the first and second outer ring elements 120, 122 may be identical, differing only in their relative orientations when operatively assembled with the inner ring element 124 to form the coupled ring assembly 102. Accordingly, the first outer ring element 120 is described below with the understanding that this description may also apply to the second outer ring element 122.

Figure 6A:
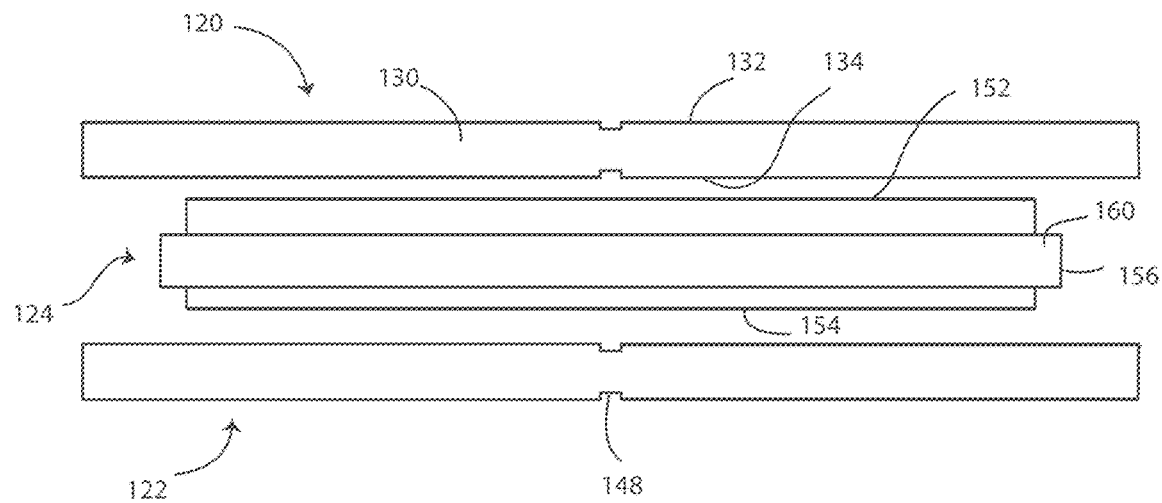
FIG. 6A is an exploded view of a coupled ring assembly of the anteversion/retroversion correction device of FIG. 2.
Figure 6B:
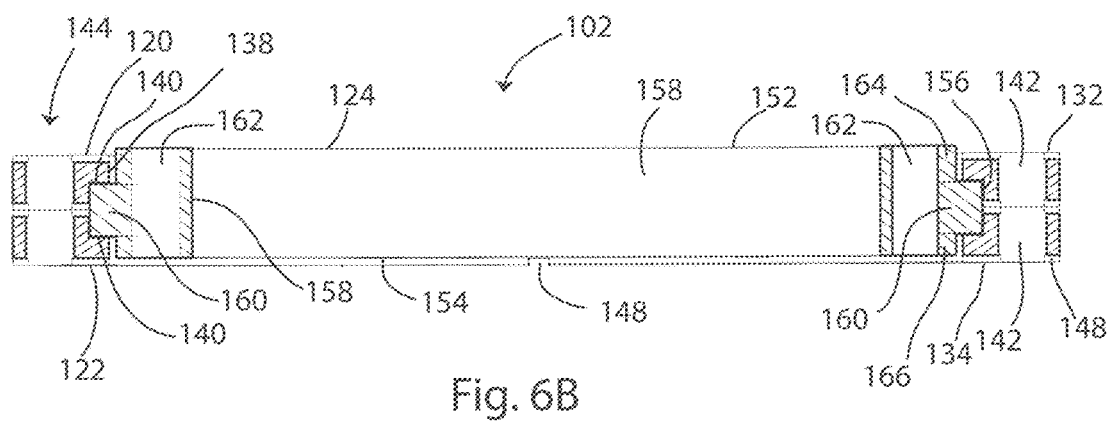
FIG. 6B is a cross-sectional view of the coupled ring assembly.

In at least one embodiment, the first outer ring element 120 may comprise an outer ring body 130 formed as a complete circle, having a superior surface 132, an inferior surface 134, an outer surface 136, and an inner surface 138, as is best seen in FIG. 6B. The inner surface 138 may include a step or notch 140, into which the inner ring element 124 may concentrically fit.

Figure 10:
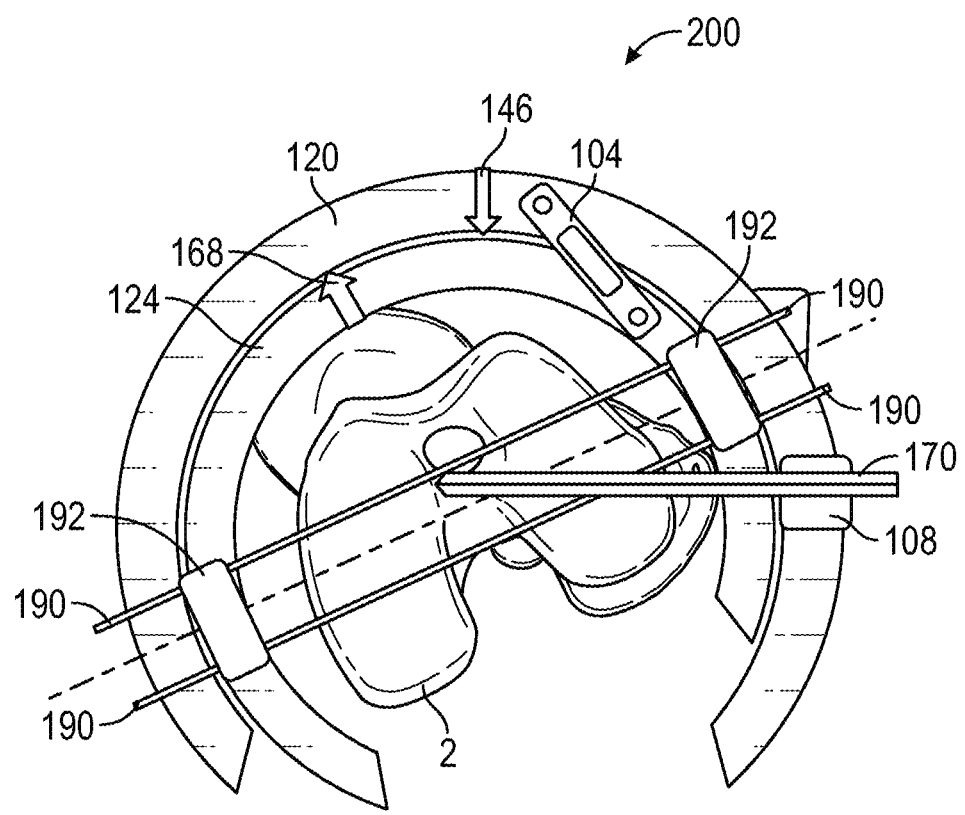
FIG. 10 is an inferior view of a femur with an alternate embodiment of an anteversion/retroversion correction device affixed to the femur, before correction of anteversion/retroversion in the femur.
Figure 11:
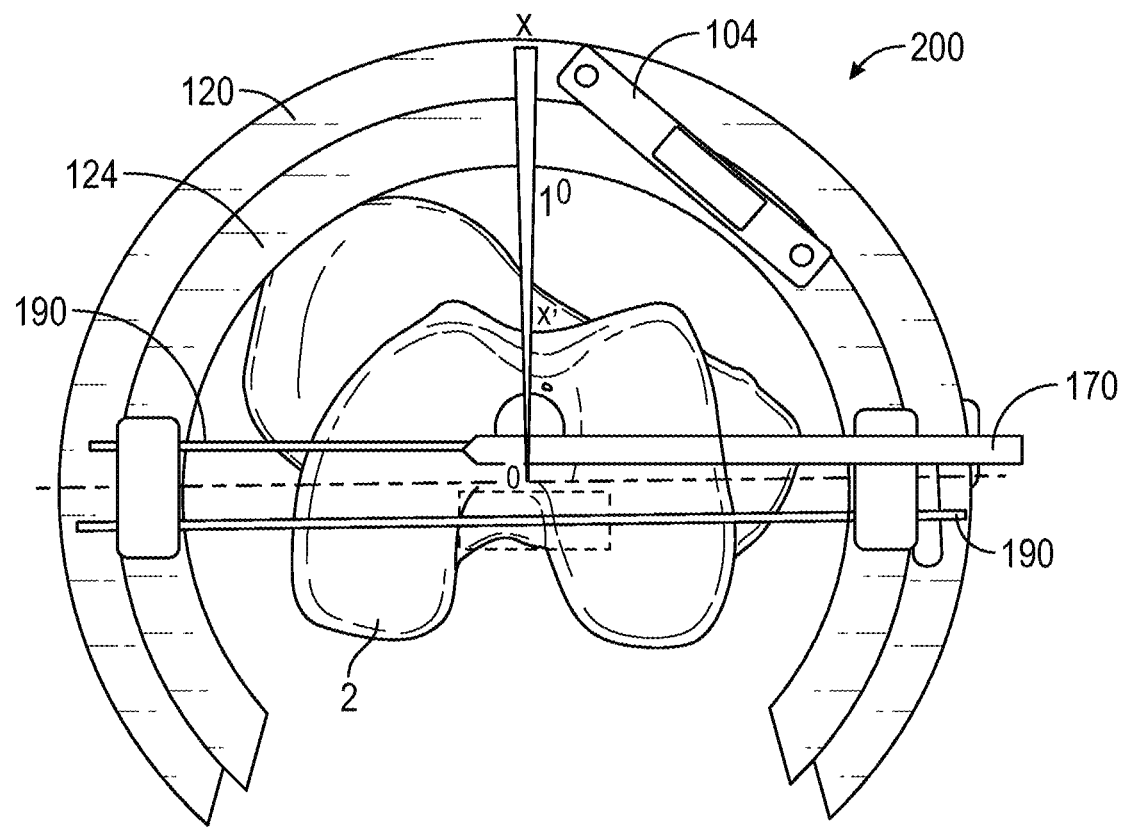
FIG. 11 is an inferior view of the femur and the anteversion/retroversion correction device of FIG. 10, during correction of anteversion/retroversion in the femur.

However, it will also be understood that in other embodiments the first outer ring element 120 may comprise a first arcuate segment and the inner ring element 124 may comprise a second arcuate segment, each of which may not form complete circles (e.g., see FIGS. 10 and 11). These first and second arcuate segments may be rotatably coupled to each other, in like fashion.

Figure 7:
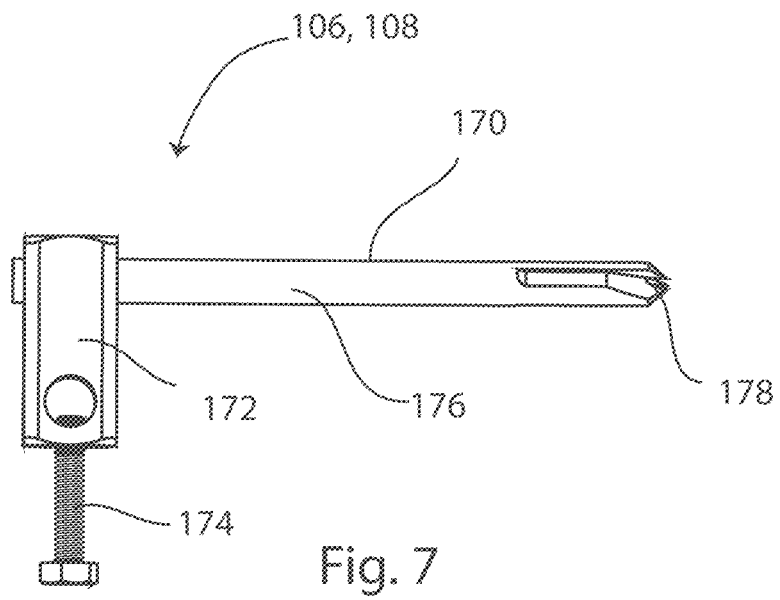
FIG. 7 is a side view of an example pin assembly of the anteversion/retroversion correction device of FIG. 2.
Figure 8:
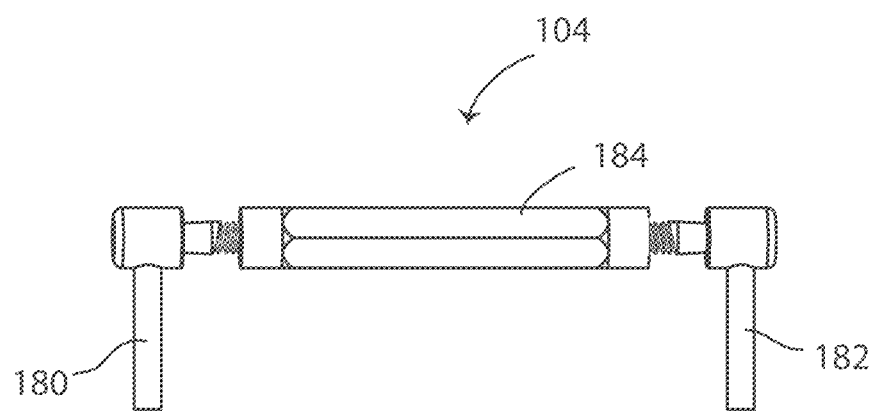
FIG. 8 is a side view of an example turnbuckle assembly of the anteversion/retroversion correction device of FIG. 2.

As shown in FIG. 6B, a plurality of outer ring apertures 142 may extend between the superior and inferior surfaces 132, 134, for receiving the first fixation pin assembly 106 and/or at least a portion of the turnbuckle assembly 104. When the first and second outer ring elements 120, 122 are operatively oriented with respect to one another, as shown in FIGS. 2, 3, 4, and 6B, the outer ring apertures 142 formed in the first and second outer ring elements 120, 122 may vertically align with each other to form a plurality of columnar passageways 144 extending through the outer ring apertures 142 formed in the first and second outer ring elements 120, 122. The plurality of columnar passageways 144 may be configured to receive a first fastener (such as the bolt 174 shown in FIG. 7), which may be configured to couple the first fixation pin assembly 106 to the outer ring assembly 103. The plurality of columnar passageways 144 may also be configured to receive a first fixation element 180 of the turnbuckle assembly 104 in order to pivotably couple of the turnbuckle assembly 104 with the outer ring assembly 103, as will be discussed in more detail below.

The first and second outer ring elements 120, 122 (and/or the inner ring element 124) may include indicia 146 which may denote degrees indicative of a range of anteversion/retroversion correction, such that the anteversion/retroversion correction can be accurately prescribed, executed, and/or tracked. The indicia 146 may include a central point, or zero degree indicator 147. The first and second outer ring elements 120, 122 may also include one or more grooves 148 or other features to assist in correctly orienting the first and second outer ring elements 120, 122 with respect to one another.

In at least one embodiment, the inner ring element 124 may comprise an inner ring body 150 formed as a complete circle and having a superior surface 152, an inferior surface 154, an outer surface 156, and an inner surface 158. A circular flange 160 may protrude outwardly from the inner ring body 150. The circular flange 160 may be received between the notches 140 formed in the first and second outer ring elements 120, 122 in order to concentrically nest the inner ring element 124 between the first and second outer ring elements 120, 122.

As shown in FIG. 6B, a plurality of inner ring apertures 162 may extend between the superior and inferior surfaces 152, 154 of the inner ring element 124. The plurality of inner ring apertures 162 may be configured to receive a second fastener (such as the bolt 174 shown in FIG. 7), which may be configured to couple the second fixation pin assembly 108 to the inner ring element 124. The plurality of inner ring apertures 162 may also be configured to receive a second fixation element 182 of the turnbuckle assembly 104 in order to pivotably couple the turnbuckle assembly 104 with the inner ring element 124.

In at least one embodiment, the height of the inner ring element 124 between its superior and inferior surfaces 152, 154 may be equal to, or substantially equal to, the combined heights of the first and second outer ring elements 120, 122.

Figure 3:
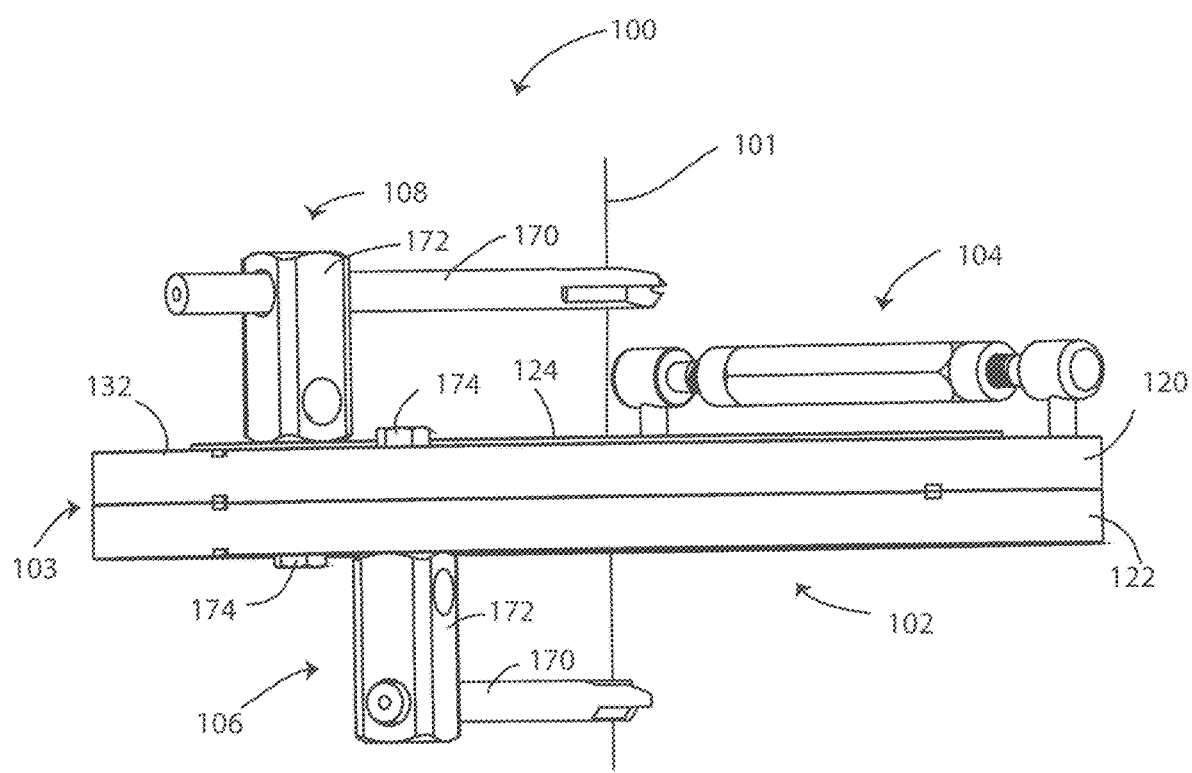
FIG. 3 is a side view of the anteversion/retroversion correction device of FIG. 2.

In at least one embodiment, a superior portion 164 of the inner ring body 150 (e.g., above the circular flange 160) may be greater in height than an inferior portion 166 of the inner ring body 150 (e.g., below the circular flange 160), as shown in FIG. 6B. Thus, as can be seen in FIGS. 3 and 6B, a portion of the inner ring element 124 may protrude above the superior surface 132 of the first outer ring element 120 when the coupled ring assembly 102 is operatively assembled together. Likewise, in this embodiment, the inferior surface 154 of the inner ring element 124 may be slightly recessed from the inferior surface of the second outer ring element 122. This height difference between the outer and inner ring elements may assist in manipulating the coupled torsional fixator 100.

When operatively assembled, as shown in FIGS. 2-5, the inner ring element 124 may be rotatable with respect to the first and second outer ring elements 120, 122, about the fixator central axis 101. A pointer 168, or another indicator, may also be present on either or both of the superior and inferior surfaces 152, 154 of the inner ring element 124 (and/or on either or both of the first and second outer ring elements 120, 122) in order to help facilitate prescribing, measuring, and tracking anteversion/retroversion correction.

Referring to FIGS. 2-5 and 7, each of the first and second fixation pin assemblies 106, 108 may generally comprise a bone fixation member, wire, K-wire, tension wire, or pin 170, a coupler 172, and a fastener or bolt 174, in at least one embodiment. The pin 170 may include a shaft 176 and a point 178 for percutaneous fixation in the patient's femur. In at least some embodiments, the pin 170 may be cannulated and/or self-tapping. It will be understood that the point 178 may comprise any suitable form known in the art for penetrating and affixing within a bone, including, but not limited to: flutes, facets, sharpened points, serrations, and other penetrating elements that are known the art. Similarly, the pin 170 may comprise a wire, K-wire, tension wire, screw, nail, post, rod, rigid cable, or any other bone fixation member that may rigid, semi-rigid, or flexible to penetrate and/or wrap around the bone in order to couple with the bone. The coupler 172 may include at least one passage (not shown in FIG. 7) for receiving the shaft 176, and a threaded opening (not shown in FIG. 7) for receiving the bolt 174. In at least one embodiment, the pin 170 and the coupler 172 may be separate members which may be coupled together. However, in other embodiments, the pin 170 and the coupler 172 may comprise a single monolithic body.

Figure 4:
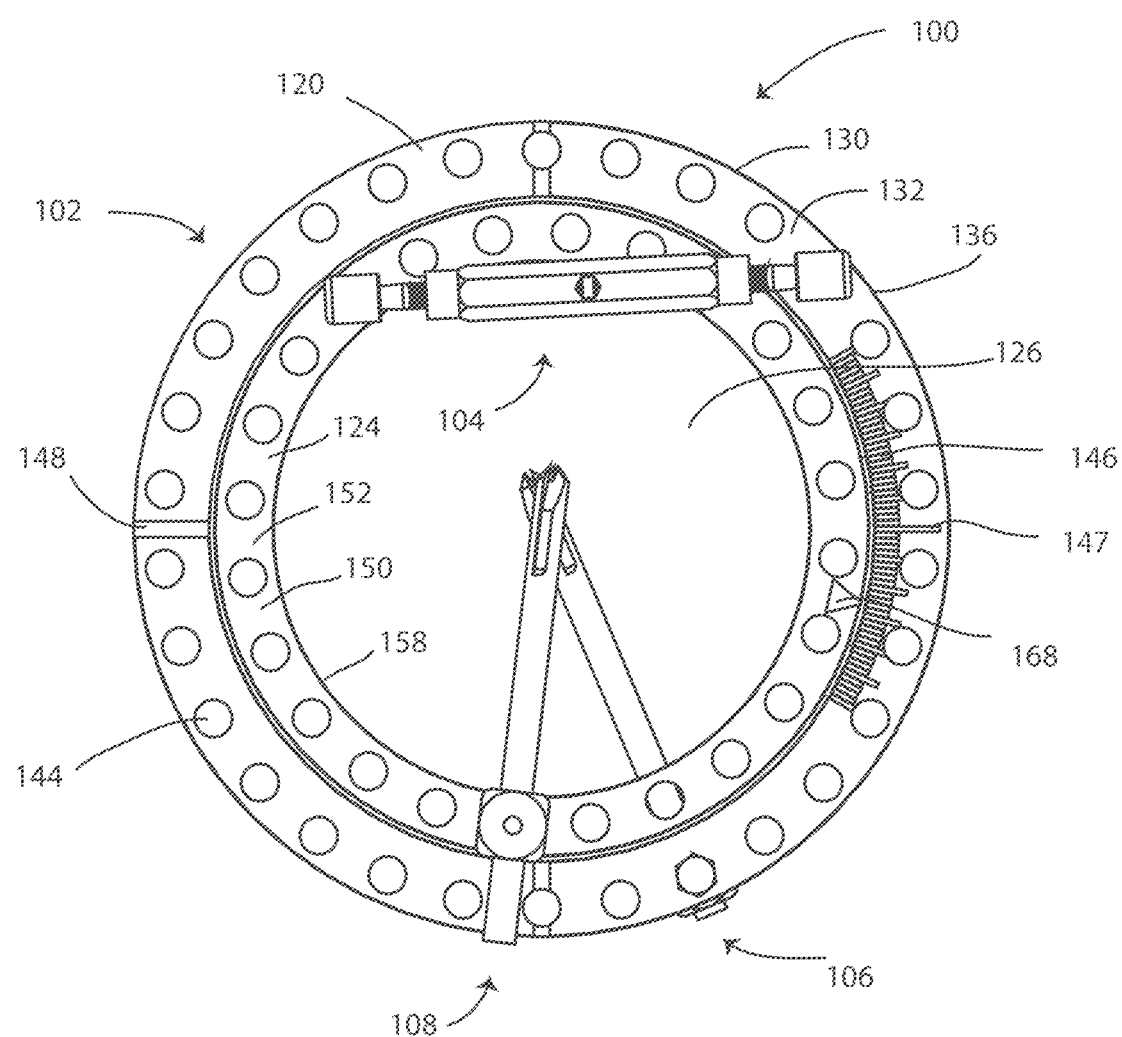
FIG. 4 is a superior view of the anteversion/retroversion correction device of FIG. 2.
Figure 5:
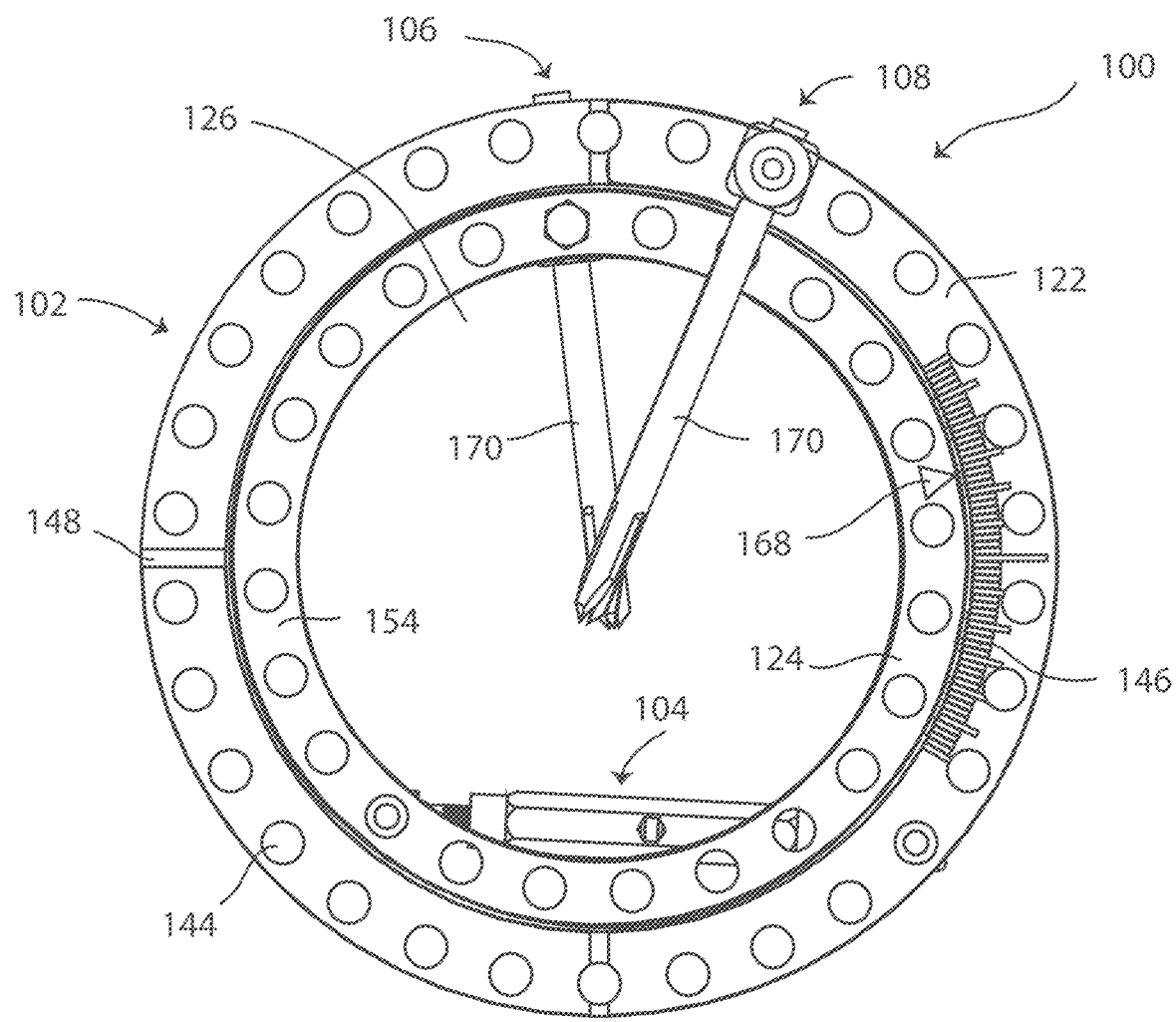
FIG. 5 is an inferior view of the anteversion/retroversion correction device of FIG. 2.

The first fixation pin assembly 106 may be coupled to the first and/or second outer ring elements 120, 122 via the bolt 174 passing through one of the columnar passageways 144 formed through the first and second outer ring elements 120, 122 (e.g., see FIG. 3). The first fixation pin assembly 106 may project inferiorly from the second outer ring element 122. Likewise, the second fixation pin assembly 108 may be coupled to the inner ring element 124 via the bolt 174 passing through one of the inner ring apertures 162 formed in the inner ring element 124. The second fixation pin assembly 108 may project superiorly from the first outer ring element 120. Both pins 170 of the first and second fixation pin assemblies 106, 108 may project inwardly relative to the outer surface 136 of the second outer ring element 122, as shown in FIGS. 4 and 5. Moreover, both pins 170 of the first and second fixation pin assemblies 106, 108 may assume any angular position with respect to each other as the outer ring assembly 103 rotates relative to the inner ring element 124.

In at least one embodiment, the coupled torsion fixator 100 may include two fixation pin assemblies. However, in other embodiments (not shown) fewer or more fixation pin assemblies may be utilized. In addition, it will be understood that the relative placement of the pin assemblies on the inner and outer rings may vary without departing from the spirit or scope of the present disclosure.

Referring to FIGS. 2-5 and 8, the turnbuckle assembly 104 may function as a control mechanism for controlling the relative position of the inner ring element 124 with respect to the first and second outer ring elements 120, 122. The turnbuckle assembly 104 may generally comprise a first fixation element 180, a second fixation element 182, and a spanning element 184 extending between the first and second fixation elements 180, 182. The spanning element 184 may be configured to rotatably couple with the first and second fixation elements 180, 182 via threading formed within the spanning element 184 and on the first and second fixation elements 180, 182.

Figure 2:
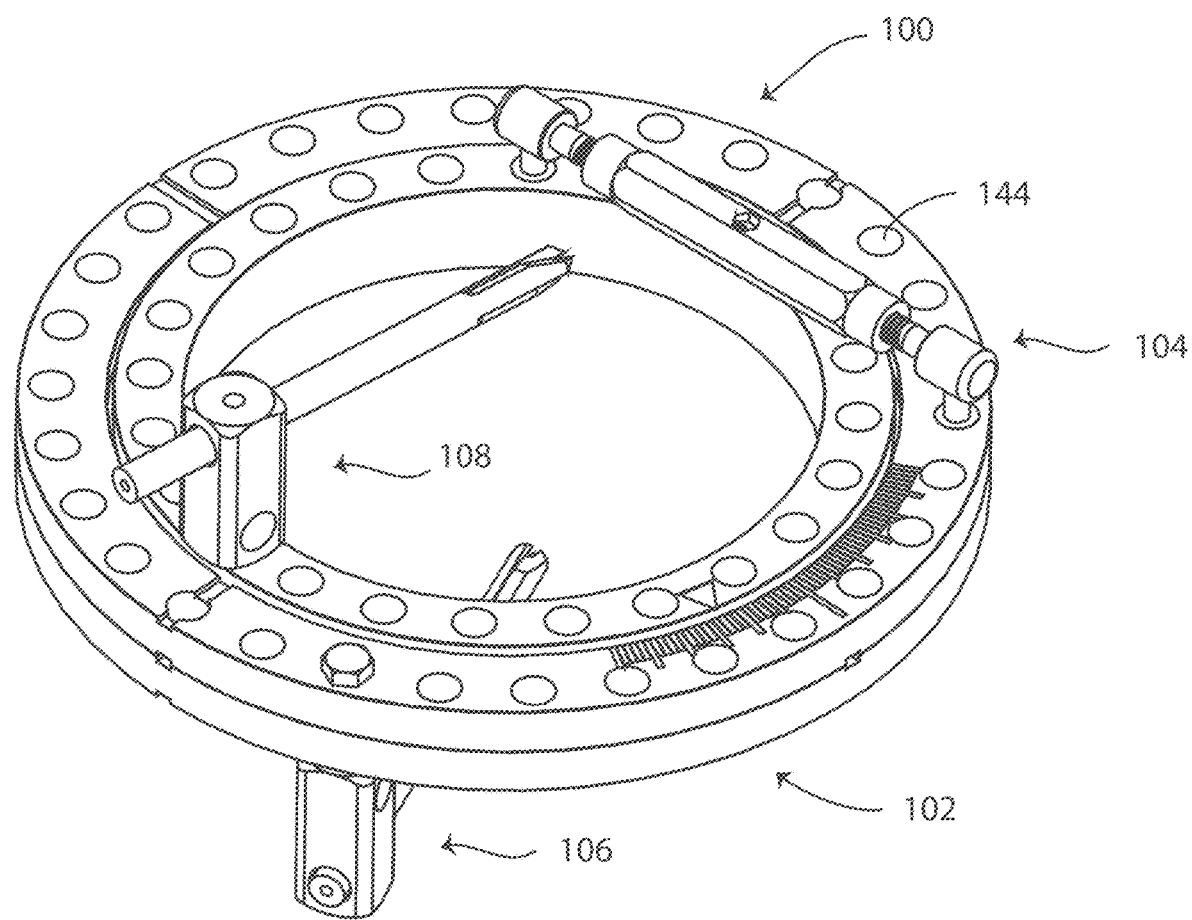
FIG. 2 is a perspective view of an anteversion/retroversion correction device.

As shown in FIG. 2, the first fixation element 180 may be attached to one of the inner or outer ring elements, and the second fixation element 182 may attached to the other of the inner or outer ring elements. Thus, the first and second fixation elements 180, 182 may be received within the columnar passageways 144 of the first and second outer ring elements 120, 122, and/or within the inner ring apertures 162 of the inner ring element 124 in order to pivotably couple the turnbuckle assembly 104 to the coupled ring assembly 102.

Once the turnbuckle assembly 104 has been pivotably coupled to the coupled ring assembly 102, the effective length of the spanning element 184 of the turnbuckle assembly 104 may be adjusted/increased (for example by rotating the spanning element 184 in a first direction, which may cause the first and second fixation elements 180, 182 to move away from each other), in order to adjust a rotational juxtaposition of the inner and outer ring elements with respect to each other to provide and maintain a corrective torsional force between the first and second fixation pin assemblies 106, 108. However, it will also be understood that any number of different mechanisms are envisioned herein for adjusting the relative positions of the outer and inner ring elements with respect to each other, such as an outrigger mechanism, a locking mechanism, a control mechanism, etc. Likewise, the effective length of the spanning element 184 of the turnbuckle assembly 104 may also be adjusted/decreased (for example by rotating the spanning element 184 in a second direction, which may cause the first and second fixation elements 180, 182 to move toward each other), in order to adjust a rotational juxtaposition of the inner and outer ring elements with respect to each other and reduce a corrective torsional force between the first and second fixation pin assemblies 106, 108.

Figure 13A:
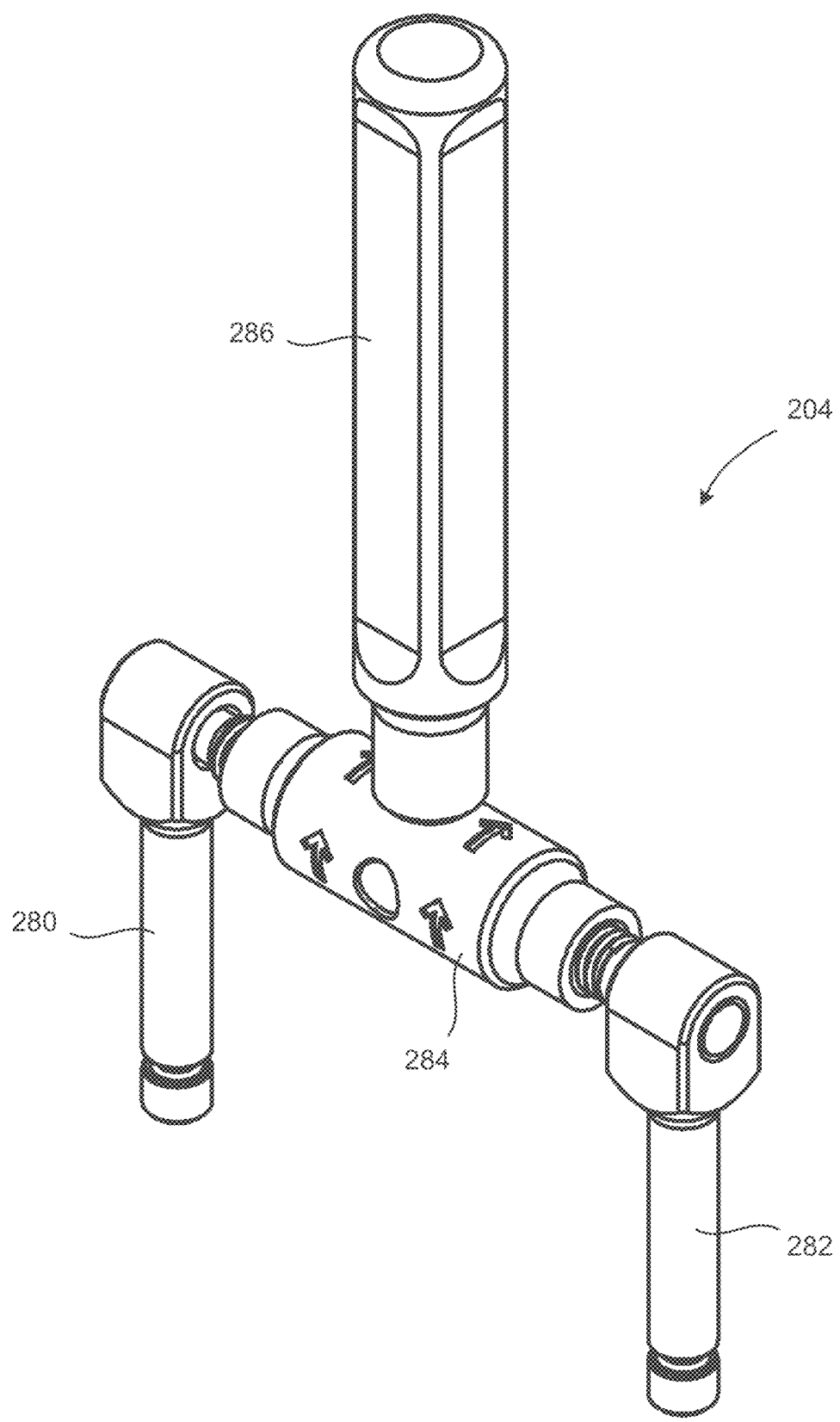
FIG. 13A is a perspective view of an example turnbuckle assembly, according to another embodiment of the present disclosure.
Figure 13B:
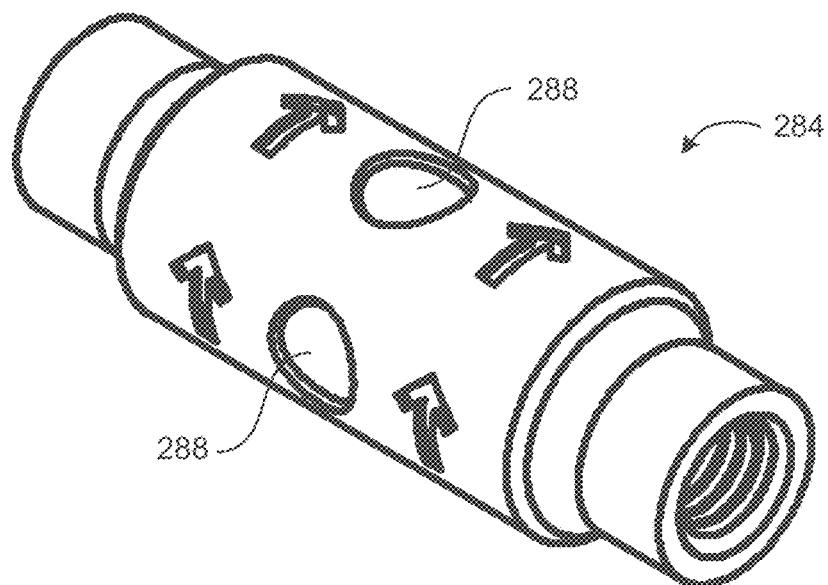
FIG. 13B is a perspective view of a spanning element of the turnbuckle assembly of FIG. 13A.
Figure 13C:
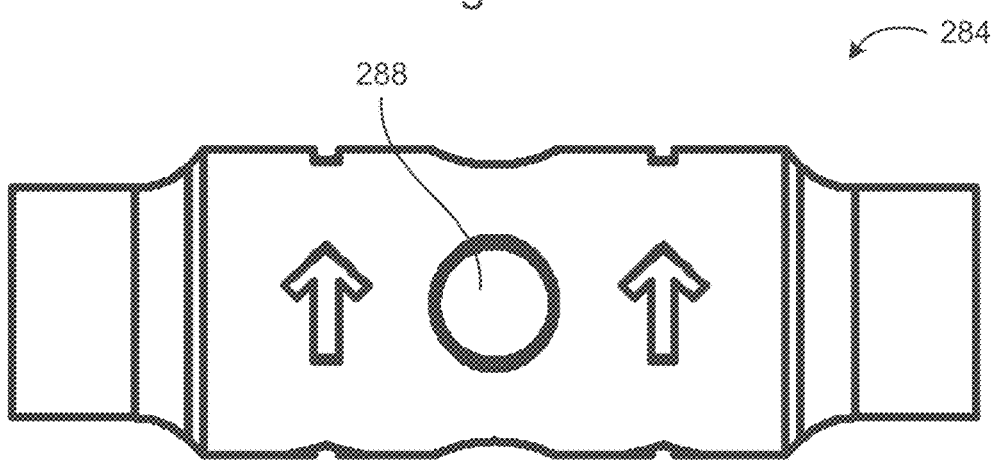
FIG. 13C is a side view of the spanning element of FIG. 13B.
Figure 13D:
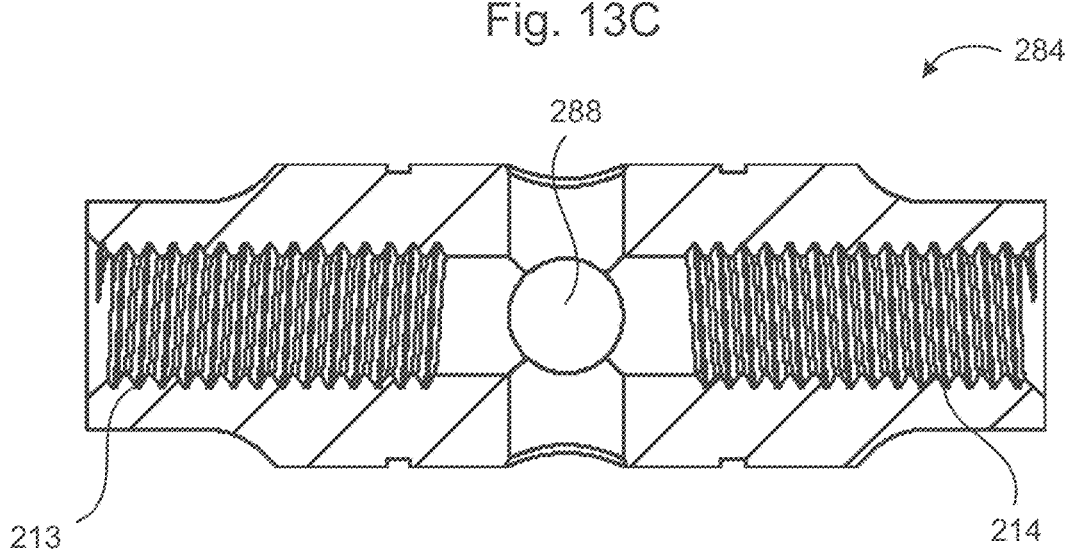
FIG. 13D is a cross-sectional side view of the spanning element of FIG. 13B.
Figure 13E:
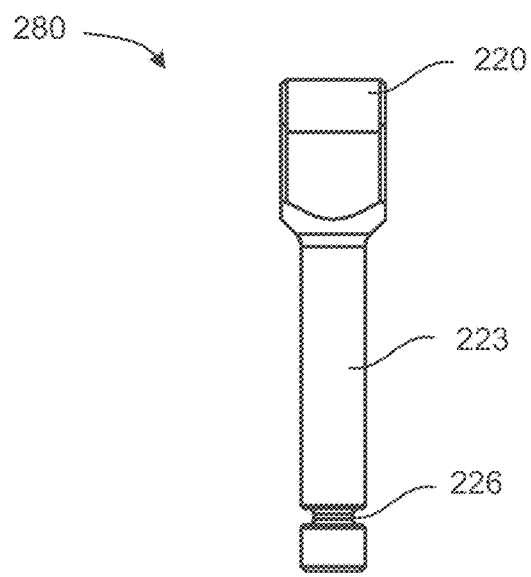
FIG. 13E is a front side view of a fixation element of the turnbuckle assembly of FIG. 13A.
Figure 13F:
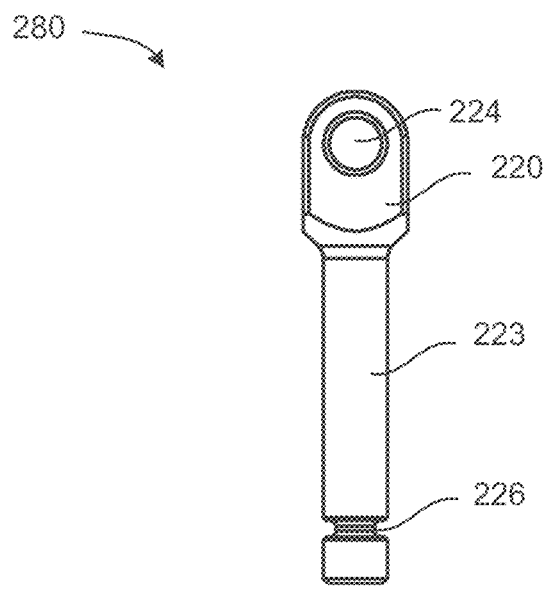
FIG. 13F is a right side view of the fixation element of FIG. 13E.
Figure 13G:
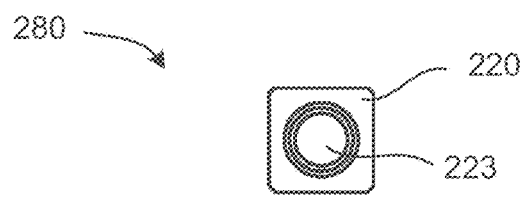
FIG. 13G is an inferior view of the fixation element of FIG. 13E.
Figure 13H:
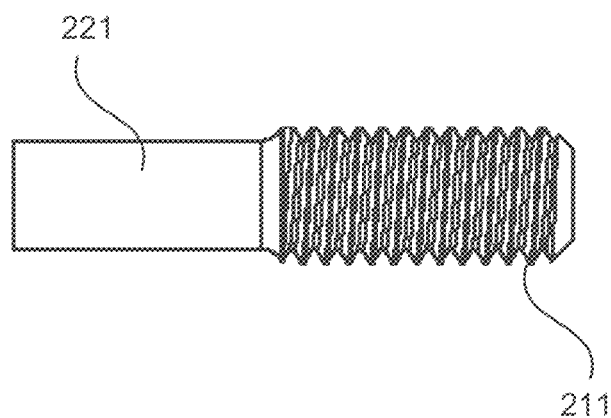
FIG. 13H is a side view of a first fixation element fastener of the turnbuckle assembly of FIG. 13A.
Figure 13I:
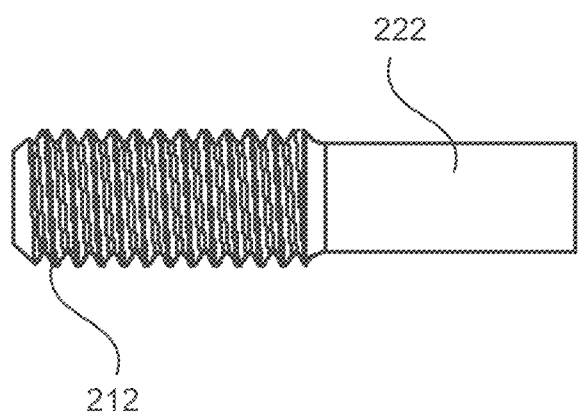
FIG. 13I is a side view of a second fixation element fastener of the turnbuckle assembly of FIG. 13A.
Figure 13J:
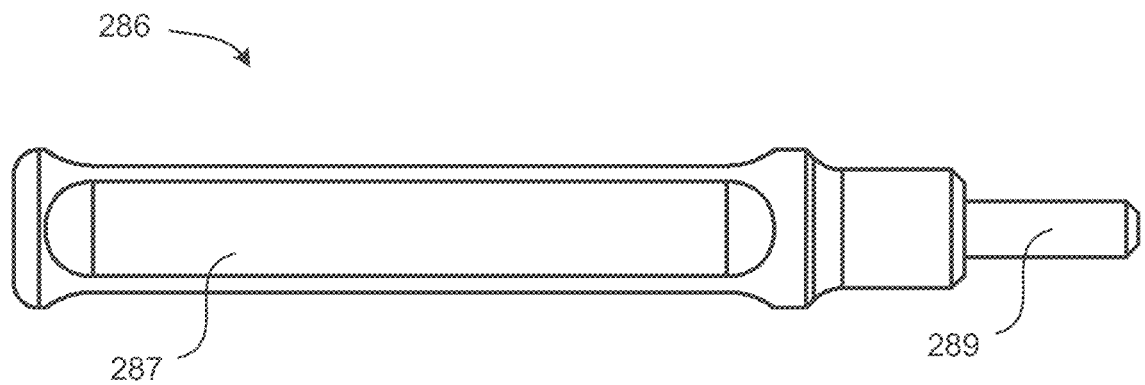
FIG. 13J is a side view of an actuator tool that may be utilized with the turnbuckle assembly of FIG. 13A.

FIGS. 13A-J illustrate a turnbuckle assembly 204, according to another embodiment of the present disclosure, which may also be utilized with the coupled torsion fixators 100, 200 described herein. Specifically, FIG. 13A is a perspective view of the turnbuckle assembly 204; FIG. 13B is a perspective view of a spanning element 284 of the turnbuckle assembly 204; FIG. 13C is a side view of the spanning element 284; FIG. 13D is a cross-sectional side view of the spanning element 284; FIG. 13E is a front side view of a first fixation element 280 of the turnbuckle assembly 204; FIG. 13F is a right side view of the first fixation element 280; FIG. 13G is an inferior view of the first fixation element 280; FIG. 13H is a side view of a first fixation element fastener 221 of the turnbuckle assembly 204; FIG. 13I is a side view of a second fixation element fastener 222 of the turnbuckle assembly 204; and FIG. 13J is a side view of an actuator tool 286 that may be utilized to actuate the spanning element 284 of the turnbuckle assembly 204.

The turnbuckle assembly 204 may likewise function as a control mechanism for controlling the relative position of the first arcuate segment (or first and second outer ring elements 120, 122) with respect to the second arcuate segment (or inner ring element 124). The turnbuckle assembly 204 may generally comprise the first fixation element 280, the second fixation element 282, a first fixation element fastener 221 coupled to the first fixation element 280, a second fixation element fastener 222 coupled to the second fixation element 282, and the spanning element 284 extending between the first and second fixation element fasteners 221, 222.

In at least one embodiment, the first and second fixation elements 280, 282 may be identical. Accordingly, the first fixation element 280 will be described below with the understanding that this description may also apply to the second fixation element 282.

With reference to FIGS. 13E-G, the first fixation element 280 may generally include a first fixation element head 220, a first fixation element aperture 224 formed through the first fixation element head 220, a first fixation element shaft 223, and a first fixation element notch 226. The first fixation element notch 226 may be utilized to couple the first fixation element 280 to the coupled ring assembly 102 (e.g., via a cotter pin (not shown), or the like). The first fixation element fastener 221 may couple with the first fixation element 280 via the first fixation element aperture 224 formed in the first fixation element head 220. However, it will be understood that in other embodiments the first fixation element 280 and the first fixation element fastener 221 may comprise a single monolithic body.

The spanning element 284 may be configured to rotatably couple with the first and second fixation element fasteners 221, 222 via threading formed within the spanning element 284 and on the first and second fixation element fasteners 221, 222. Specifically, the first fixation element fastener 221 may include first threading 211, the second fixation element fastener 222 may include second threading 212, and the spanning element 284 may include third threading 213 configured to engage the first threading 211 of the first fixation element fastener 221, and fourth threading 214 configured to engage the second threading 212 of the second fixation element fastener 222.

Once the turnbuckle assembly 204 has been pivotably coupled to the first arcuate segment (or first and second outer ring elements 120, 122) and the second arcuate segment (or inner ring element 124), the effective length of the spanning element 284 of the turnbuckle assembly 204 may be adjusted/increased (for example by rotating the spanning element 284 in a first direction, which may cause the first and second fixation elements 280, 282 to move away from each other) in order to adjust a rotational juxtaposition of the first and second arcuate segments with respect to each other to provide and maintain a corrective torsional force between the first and second fixation pin assemblies 106, 108. Likewise, the effective length of the spanning element 284 of the turnbuckle assembly 204 may also be adjusted/decreased (for example by rotating the spanning element 284 in a second direction, which may cause the first and second fixation elements 280, 282 to move toward each other), in order to adjust a rotational juxtaposition of the first and second arcuate segments with respect to each other and reduce a corrective torsional force between the first and second fixation pin assemblies 106, 108. The spanning element 284 may be rotated by inserting the actuator tool engagement feature 289 of the actuator tool 286 into one of the spanning element apertures 288, and then applying a force to the handle 287 of the actuator tool 286 in order to rotate the spanning element 284 in either of the first or second directions. In this manner, the turnbuckle assembly 204 (or other control mechanism) can enable fixation of the second arcuate segment in any of a plurality of orientations relative to the first arcuate segment in order to control an orientation of the first pin with respect to the second pin and exert torsional force on an intact bone between a proximal bone segment and a distal bone segment of the intact bone, thereby externally reducing anteversion/retroversion of the intact bone.

Figure 9:
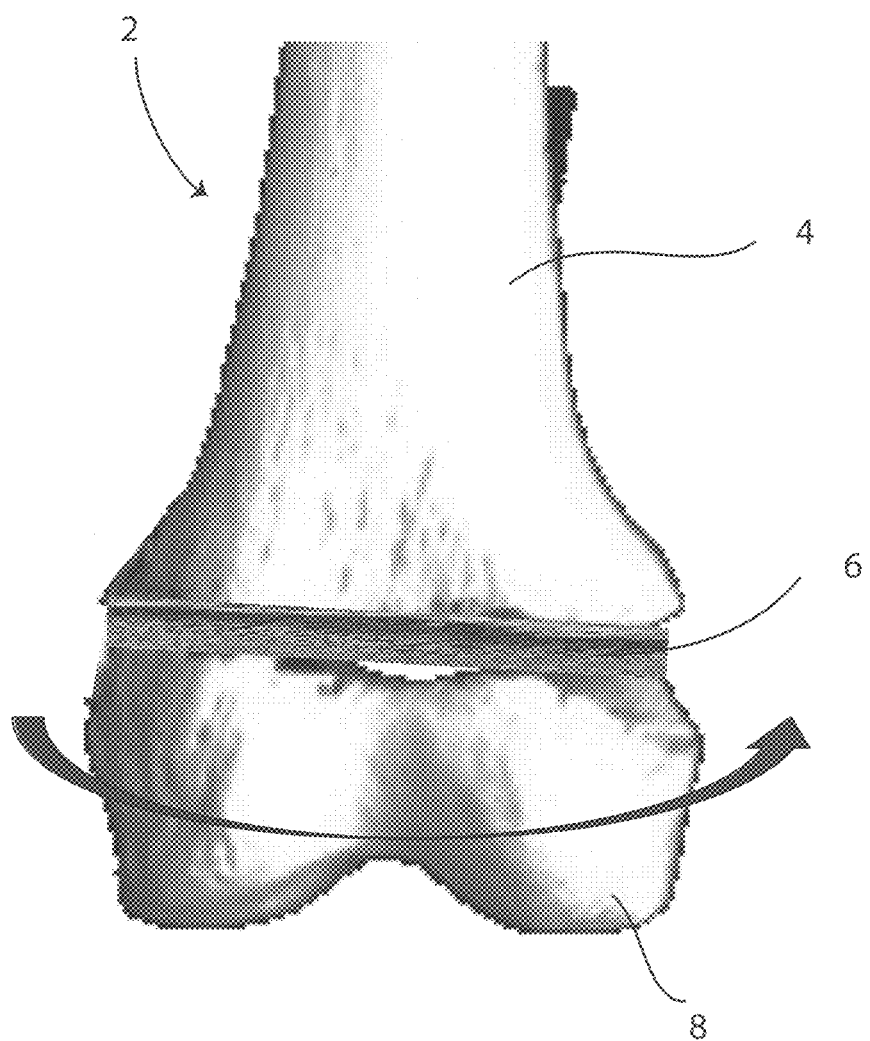
FIG. 9 is an anterior view of a femur distal end, illustrating the location of a physeal growth plate, and including an arrow indicating the direction of torque necessary to correct anteversion/retroversion of the femur.

In one method of use, the coupled torsional fixator 100 may be positioned to encircle a femur 2 requiring anteversion/retroversion correction. Prior to positioning the coupled torsional fixator 100, the pins 170 may be drawn out of the way in their respective couplers, or removed entirely to allow the femur 2 to pass through the ring assembly bore 126. The coupled torsional fixator 100 may be positioned at a desired location relative to the femur 2, for example at the level of the physis 6, or physeal growth plate, of the femur 2, as illustrated in FIG. 9. With the coupled torsional fixator 100 at the desired position, the pin 170 of the first fixation pin assembly 106 may be percutaneously secured into the femur 2 on one side of the physis 6, for example below the physis 6 in the distal bone segment, distal segment of the intact bone, or distal femur 8. The pin 170 of the second fixation pin assembly 108 may be percutaneously secured into the femur 2 on the opposite side of the physis 6, for example above the physis 6 in the proximal bone segment, proximal segment of the intact bone, or femur shaft 4. The pins 170 may be installed at a selected first angle or initial angle relative to one another from a superior or inferior perspective. In an embodiment, if the amount of correction desired is 30°, the second fixation pin assembly 108 may be positioned to hold its pin 170 at a 30° angle relative to the first pin 170 of the first fixation pin assembly 106. At this initial position, the pointer 168 on the coupled ring assembly 102 may point at a location relative to the indicia 146 on the coupled ring assembly 102 to indicate an amount of anteversion/retroversion correction.

The coupled torsional fixator 100 can be gradually adjusted by actuation of the turnbuckle assembly 104, 204 to gradually increase anteversion/retroversion correction over time. The spanning element 184, 284 may be rotated to adjust the length of the turnbuckle assembly 104, 204 and thus rotate the first arcuate segment or first and second outer ring elements 120, 122 relative to the second arcuate segment or inner ring element 124. This will also adjust a distance/angle between the first and second fixation pin assemblies 106, 108 and their respective pins. In doing so, the distal femur 8 may be gradually twisted relative to the femur shaft 4 to correct anteversion/retroversion.

In an embodiment of the method, the rate of anteversion/retroversion correction may be 1 degree per day. In another embodiment of the method, the rate of anteversion/retroversion correction may be less than 1 degree per day (e.g., 0.5 degrees per day, etc.). In yet another embodiment of the method, the rate may be more than 1 degree per day (e.g., 1.5 degrees per day, etc.).

In some embodiments, the turnbuckle assembly 104, 204 may be actuated once per day or once every couple of days (or longer), etc. The turnbuckle assembly 104, 204 may also be actuated more than once per day to attain anteversion/retroversion correction (e.g., the turnbuckle assembly 104, 204 may be actuated two times per day, three times per day, etc.). In some embodiments, the rate of anteversion/retroversion correction that is implemented may vary from day to day.

In some embodiments of the method, the initial angle of the pins 170 relative to one another may vary, and the pins 170 need not be parallel to one another at the completion of the derotation process, or at any point during the derotation process. As anteversion/retroversion correction proceeds, the pins 170 may gradually move toward (or away from) one another until they reach a desired or selected second angle, in at least some embodiments. In an embodiment, the selected second angle may be 0°, such that the pins 170 are vertically aligned from a superior or inferior perspective and they are parallel, or substantially parallel, relative to one another. At this juncture, the pointer 168 may be pointing at the zero degree indicator(s) of the indicia 146. After correction of the anteversion/retroversion, the torsional fixator 100 may be removed from the patient.

Figure 12:
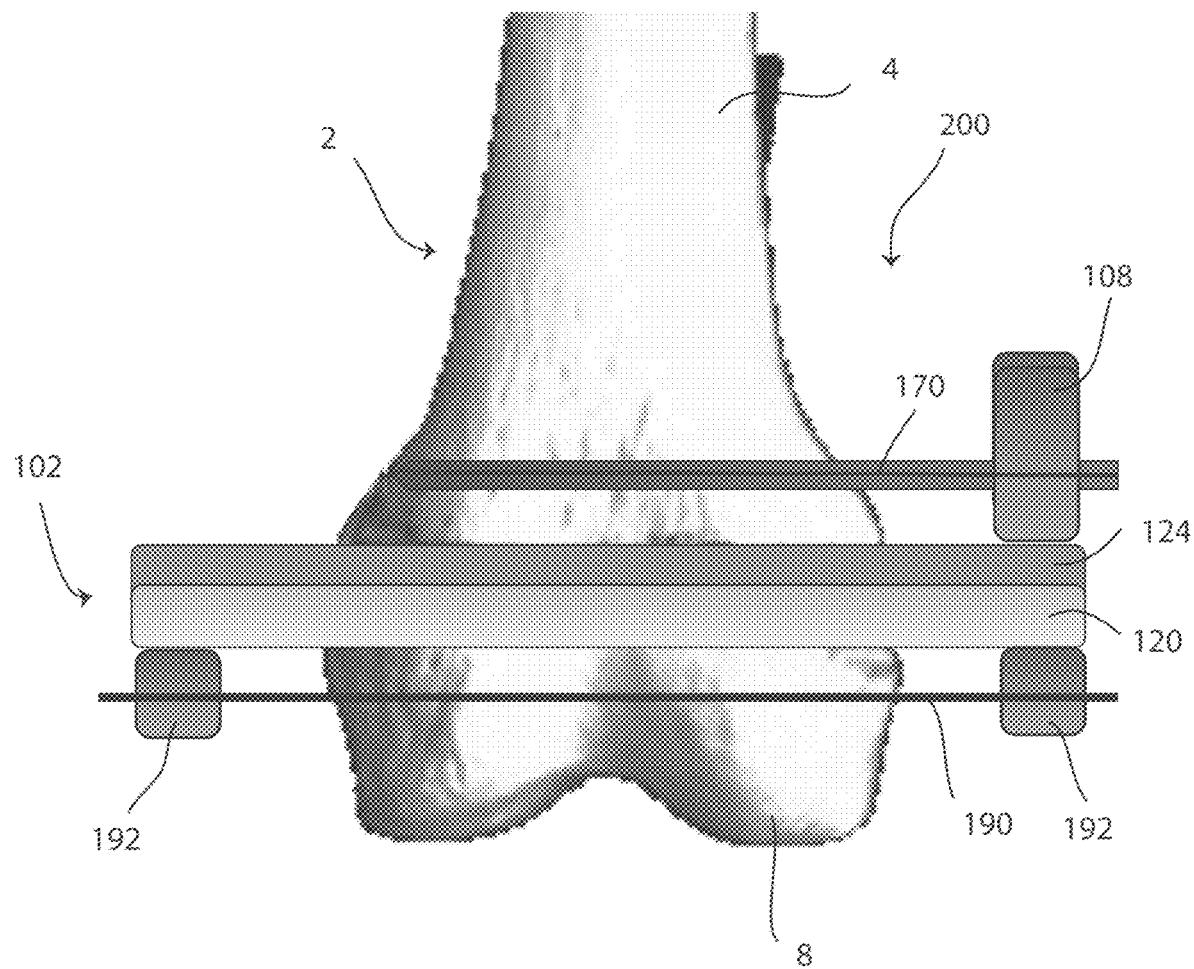
FIG. 12 is an anterior view of the femur and the anteversion/retroversion correction device of FIG. 10, after correction of anteversion/retroversion in the femur.

Referring to FIGS. 10-12, in an alternate embodiment of the disclosure, at least one of the first and second pins may comprise one or more wires 190 that are secured between two opposing couplers 192 that are positioned on opposite sides of the coupled ring assembly 102. For example, the two opposing couplers 192 may be coupled on opposite sides of the first arcuate segment (or inner ring element 124), or they may be coupled on opposite sides of the second arcuate segment (or first and second outer ring elements 120, 122), or they may be coupled on opposite sides of the outer ring assembly 103, etc. In this manner, the one or more wires 190 may extend across the coupled ring assembly 102 between the two opposing couplers 192 which are attached to the coupled ring assembly 102.

FIGS. 10-12 illustrate one example of such an alternate embodiment, including a coupled torsional fixator 200 secured to the femur 2. One or more wires 190 may extend through the femur 2 below the physis and may be secured to the second arcuate segment or inner ring element 124, as shown in this example. A pin 170 may also be secured to the femur 2 above the physis and the pin 170 may be secured to the first arcuate segment or first outer ring element 120. The turnbuckle assembly 104 may control the relative movement between the inner ring element 124 and the first outer ring element 120. In FIG. 11, correction of the anteversion/retroversion has almost been completed, with about one degree of correction remaining. In FIG. 12, correction of the anteversion/retroversion has been completed, and the pin 170 is shown parallel with the wires 190, at least in this example.

Figure 14:
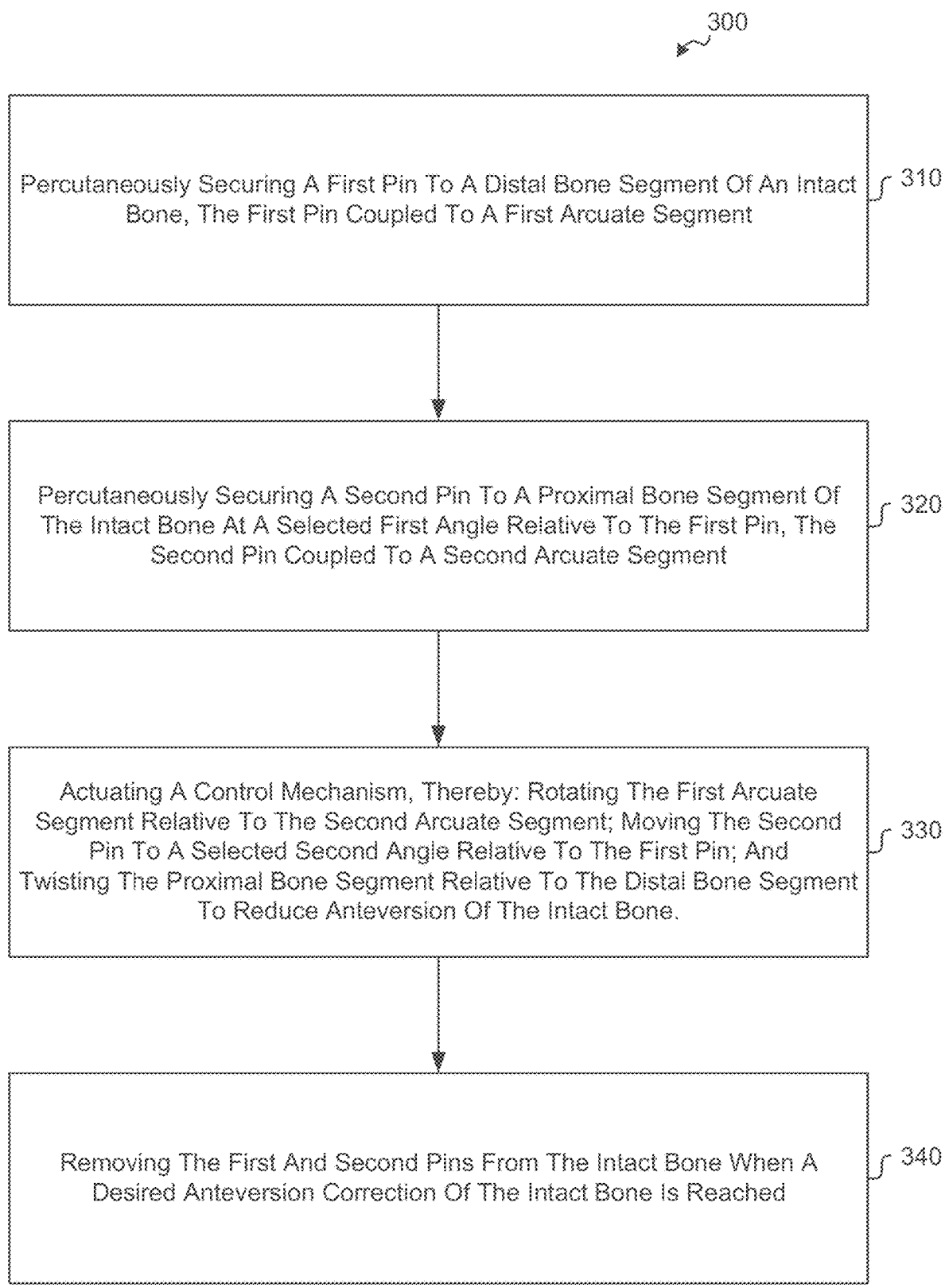
FIG. 14 is a flow chart of a method for external anteversion/retroversion correction of an intact bone, according to an embodiment of the present disclosure.

FIG. 14 illustrates a flow chart of a method 300 for external anteversion/retroversion correction of an intact bone, according to an embodiment of the present disclosure. In general, the method 300 may utilize any of the devices or device components described herein, in any combination or configuration. In one example, the method 300 may utilize a device comprising a first arcuate segment and a second arcuate segment rotatably coupled together, a first pin coupled to the first arcuate segment, a second pin coupled to the second arcuate segment, and a control mechanism coupled to the first and second arcuate segment.

The method may begin with a step 310 in which a first pin may be percutaneously secured to a distal bone segment of an intact bone. The first pin may also be coupled to the first arcuate segment, either directly, or indirectly via a first fixation assembly.

Once the first pin has been percutaneously secured to the distal bone segment of the intact bone, the method 300 may proceed to a step 320 in which a second pin may be percutaneously secured to a proximal bone segment of the intact bone at a selected first angle relative to the first pin. The second pin may also be coupled to the second arcuate segment, either directly, or indirectly via a second fixation assembly. Moreover, in some embodiments the first arcuate segment may comprise an outer ring and the second arcuate segment may comprise an inner ring concentrically and rotatably coupled to the outer ring.

Once the second pin has been percutaneously secured to the proximal bone segment of the intact bone, the method 300 may proceed to a step 330 in which the control mechanism may be actuated, thereby: (1) rotating the first arcuate segment relative to the second arcuate segment; (2) moving the second pin to a selected second angle relative to the first pin; and; (3) twisting the proximal bone segment relative to the distal bone segment to reduce anteversion/retroversion of the intact bone.

In some embodiments, actuating the control mechanism may further comprise incrementally actuating the control mechanism over a period of time, thereby: (1) rotating the inner ring relative to the outer ring to a plurality of different positions; (2) moving the second pin to a plurality of different angles relative to the first pin; and (3) gradually twisting the proximal bone segment relative to the distal bone segment to reduce anteversion/retroversion of the intact bone over the period of time.

In some embodiments, actuating the control mechanism may further comprise rotating at least a portion of the control mechanism, thereby: (1) increasing a length of the control mechanism; (2) rotating the inner ring relative to the outer ring; (3) moving the second pin to a selected second angle relative to the first pin; and (4) twisting the proximal bone segment relative to the distal bone segment to reduce anteversion/retroversion of the intact bone.

In some embodiments, rotating the at least a portion of the control mechanism in a first direction increases the length of the control mechanism, and rotating the at least a portion of the control mechanism in a second direction decreases the length of the control mechanism.

Once the control mechanism has been actuated, the method 300 may proceed to a step 340 in which the first and second pins may be removed from the intact bone when a desired amount of anteversion/retroversion correction has been reached, and the method 300 may end.

Figure 15:
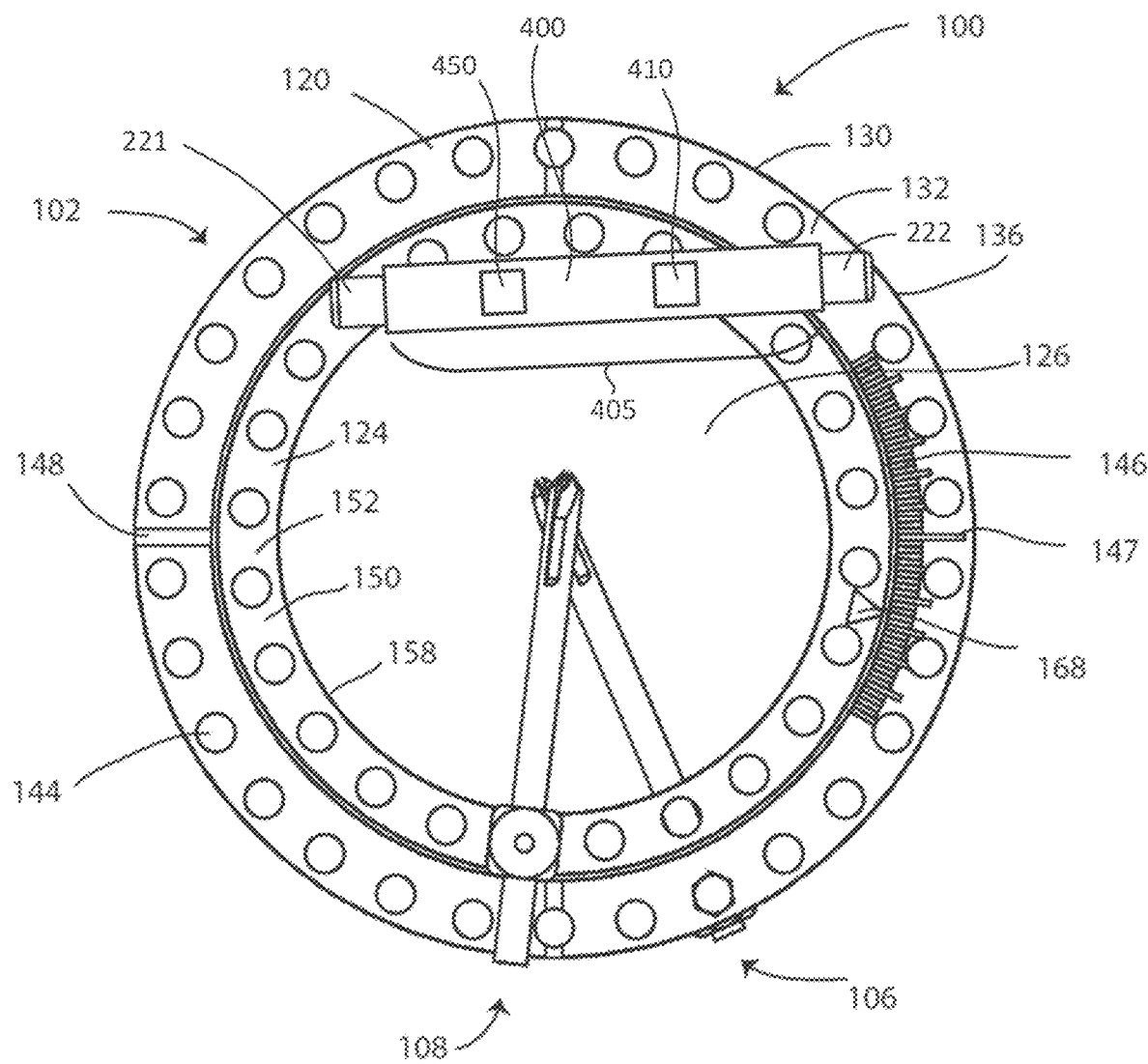
FIG. 15 is a top view of the coupled torsional fixator shown in FIGS. 2-5 coupled with an automated control mechanism 400.

FIG. 15 illustrates an automated turnbuckle assembly or automated control mechanism 400 that may be utilized with any of the coupled torsion fixators 100, 200 that are described or contemplated herein, according to another embodiment of the present disclosure. For example, FIG. 15 illustrates the automated control mechanism 400 attached to the coupled torsion fixator 100 shown in FIGS. 2-8, as one non-limiting example. However, it will also be understood that the automated control mechanism 400 may be utilized with the coupled torsion fixator 200 shown in FIGS. 10-12 and/or with other coupled torsion fixator embodiments that are described or contemplated herein.

In some embodiments, the automated control mechanism 400 may utilize the first fixation elements (180, 280), the first fixation element fastener 221, the second fixation elements (182, 282), and/or the second fixation element fastener 222, as previously described herein.

In some embodiments, the automated control mechanism 400 may be configured to rotatably couple with the first and second fixation element fasteners 221, 222 via threading formed within the automated control mechanism 400 that may be configured to engage with the threading formed on the first and second fixation element fasteners 221, 222, as previously described herein.

Once the automated control mechanism 400 has been pivotably coupled to the outer ring assembly 103 (or first frame member, or first arcuate segment) and the inner ring element 124 (or second frame member, or second arcuate segment), the effective length 405 of the automated control mechanism 400 may be adjusted (e.g., increased and/or decreased) in an automated fashion to provide and maintain a corrective torsional force between the first and second fixation pin assemblies 106, 108. In this manner, the automated control mechanism 400 can enable fixation of the outer ring assembly 103 in any of a plurality of orientations relative to the inner ring element 124 in an automated fashion to control an orientation of the first pin with respect to the second pin and exert a torsional force on an intact bone between a proximal bone segment and a distal bone segment of the intact bone, thereby externally reducing anteversion/retroversion of the intact bone over time.

In some embodiments, the automated control mechanism 400 may be configured to automatically adjust an effective length 405 of the automated control mechanism 400 to control an angular position of the first pin with respect to the second pin and impart the torsional force to the intact bone to externally reduce anteversion/retroversion of the intact bone, as previously described herein.

In some embodiments, the automated control mechanism 400 may be associated with a power source 410 that may be configured to deliver power to the automated control mechanism 400 to enable the automated control mechanism 400 to automatically adjust its effective length 405 in an automated fashion.

In some embodiments, the power source 410 may comprise a container of pressurized gas, liquid, and/or solid or semi-solid material(s) that may be configured to impart a mechanical force to or within the automated control mechanism 400 in order to adjust the effective length 405 of the automated control mechanism 400 over time in an automated fashion.

In some embodiments, the power source 410 may comprise a mechanical spring, a torsion member, a tension member, and/or any other device or structure that is capable of storing mechanical power and/or imparting a mechanical force to or within the automated control mechanism 400 to adjust the effective length 405 of the automated control mechanism 400 over time in an automated fashion. For example, in some embodiments the power source 410 may comprise a structure such as a spiral torsion spring (e.g., similar to a clock mainspring) that may be configured to store mechanical power therein that can be transferred to the automated control mechanism 400 (e.g., via gears, etc.) in order to adjust the effective length 405 of the automated control mechanism 400 over time in an automated fashion.

In some embodiments, the power source 410 may also comprise a self-winding mechanism (e.g., a rotatable weight that is configured to wind the spiral torsion spring as the patient moves about) to replenish the mechanical power that is stored within the spiral torsion spring and maintain (and/or increase) the torsional force applied to the intact bone by the automated control mechanism 400 during the anteversion/retroversion correction process.

In some embodiments, the automated control mechanism 400 may also comprise a one-way ratcheting mechanism (not shown) that may be configured to allow increases in the effective length 405 of the automated control mechanism 400 along a first direction, and/or prevent any subsequent decreases in the effective length 405 of the automated control mechanism 400 along a second direction (opposite the first direction) during the anteversion/retroversion treatment process. However, it will also be understood that the one-way ratcheting mechanism may be selectively disengaged (e.g., by an operator) to allow the effective length 405 of the automated control mechanism 400 to decrease and/or facilitate removal of the coupled torsional fixators 100, 200 from the patient.

In some embodiments, the power source 410 may comprise chemical and/or electrical energy that may be transformed into mechanical force to adjust the effective length 405 of the automated control mechanism 400 over time in an automated fashion. For example, the power source 410 may comprise a battery (and/or any other chemical, hydraulic, and/or electric power source) connected to a stepper motor that may be configured to transform the electric power received from the battery into mechanical force to adjust the effective length 405 of the automated control mechanism 400 over time in an automated fashion.

In some embodiments, the automated control mechanism 400 may be configured to receive power from the power source 410, rotate the first frame member to a desired relative rotational position with respect to the second frame member, and position the first bone fixation member at a desired/second angle relative to the second bone fixation member to exert torsional force on the intact bone between the distal segment and the proximal segment, thereby externally reducing anteversion/retroversion of the intact bone.

Figure 16:
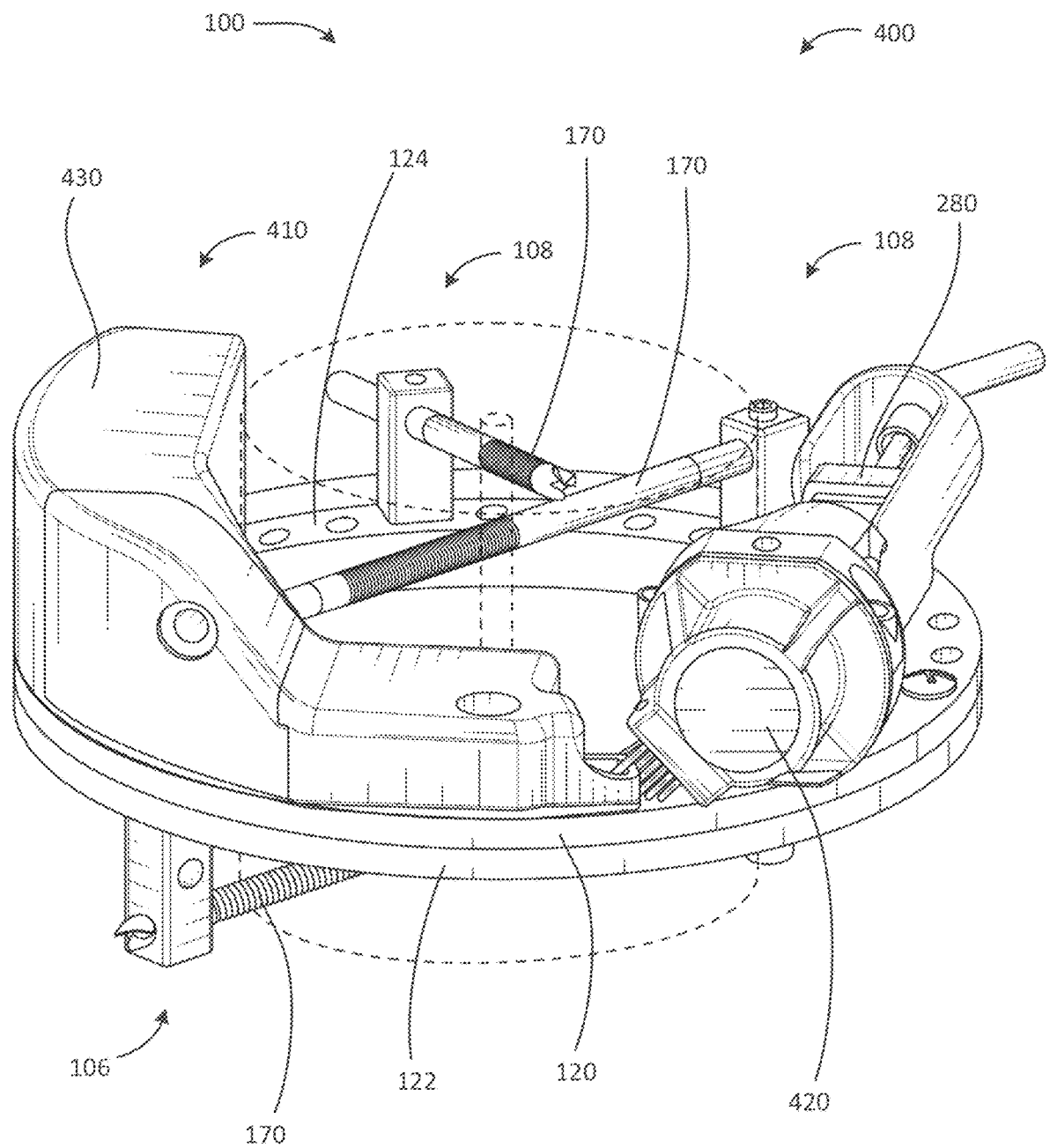
FIG. 16 is a perspective view of the coupled torsional fixator shown in FIGS. 2-5 coupled with a stepper motor 420 at a first rotational position.
Figure 17:
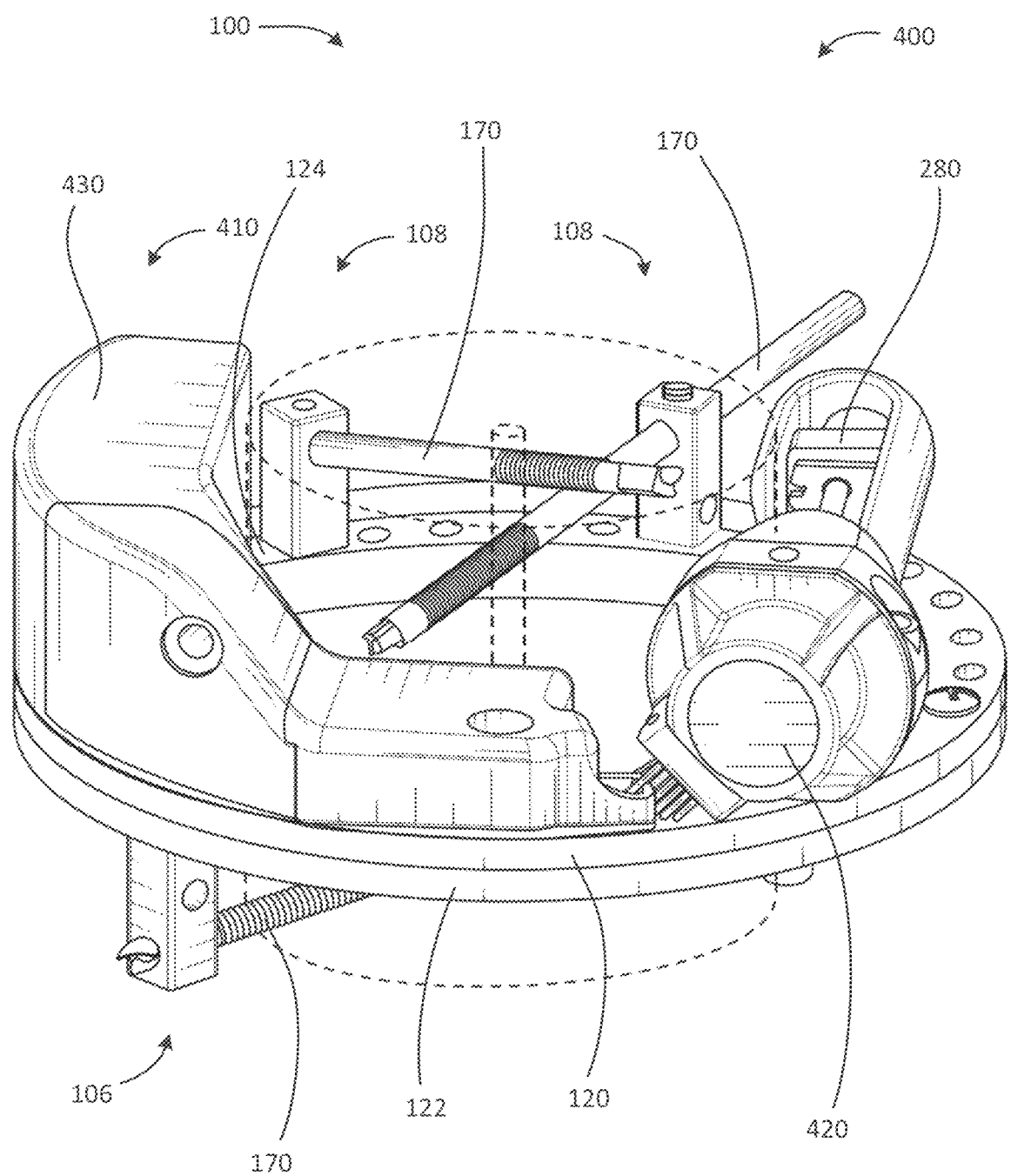
FIG. 17 is a perspective view of the coupled torsional fixator and stepper motor assembly of FIG. 16 at a second rotational position.
Figure 18:
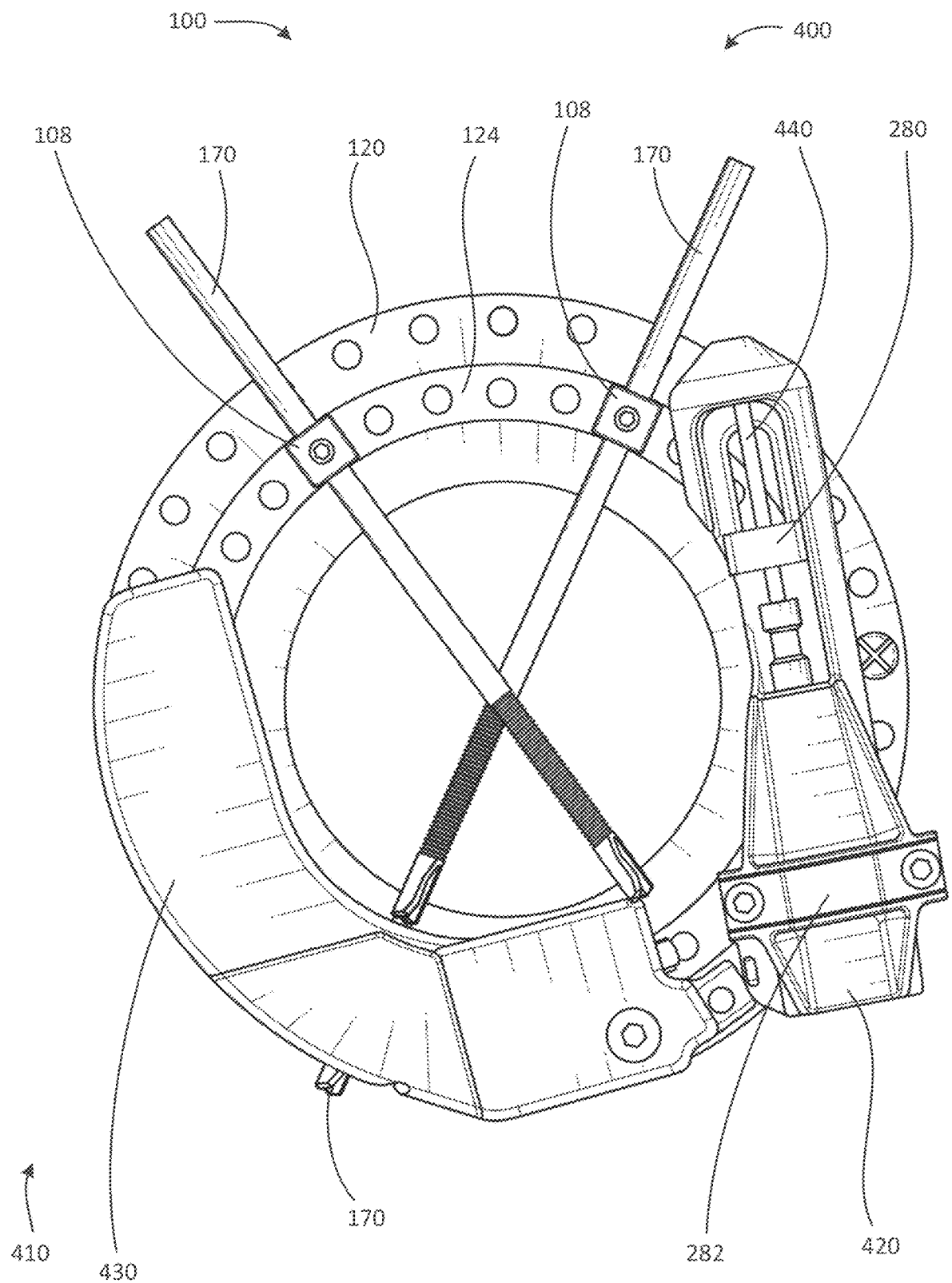
FIG. 18 is a top view of the coupled torsional fixator and stepper motor assembly of FIG. 16 at the first rotational position.
Figure 19:
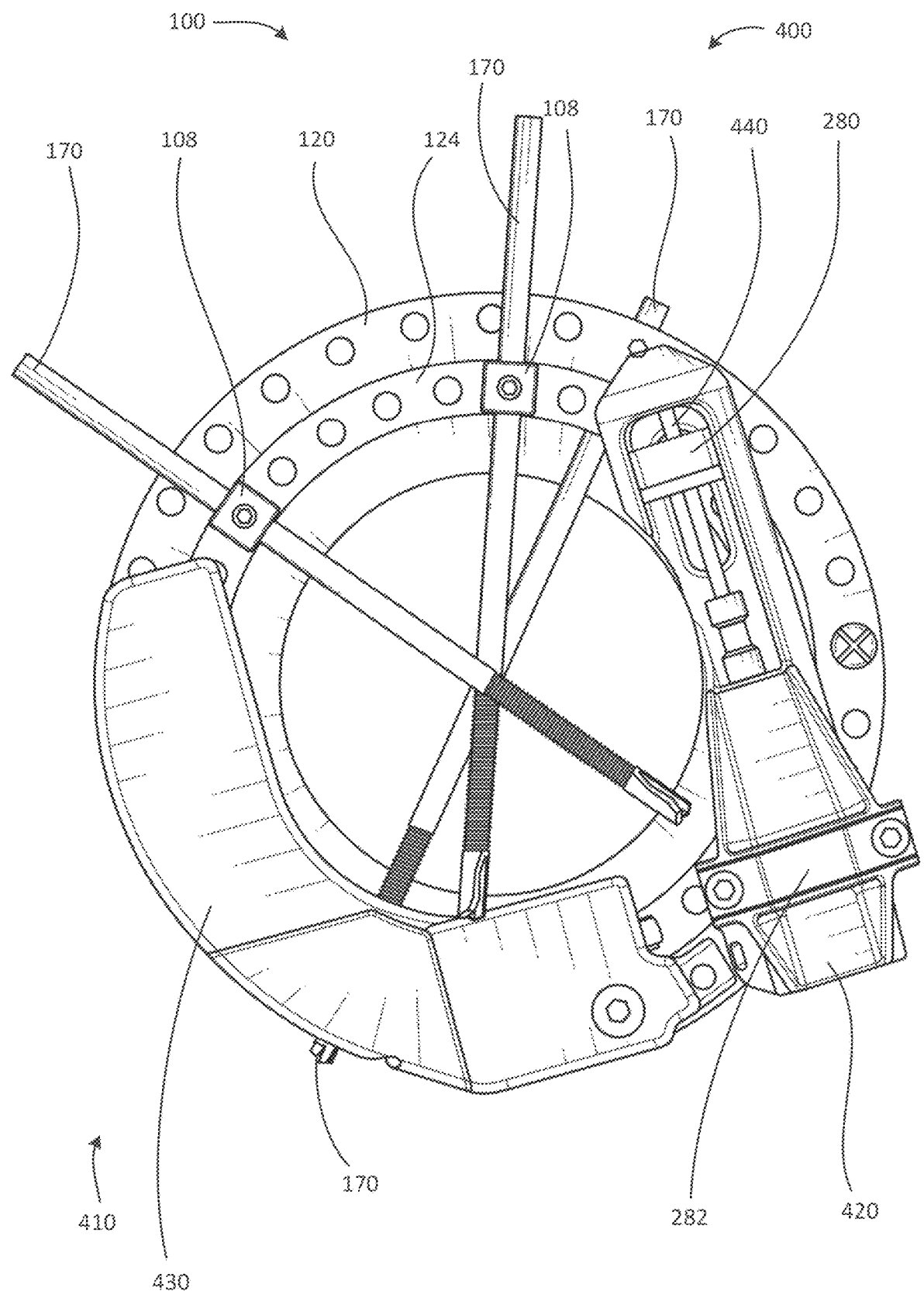
FIG. 19 is a top view of the coupled torsional fixator and stepper motor assembly of FIG. 16 at the second rotational position.
Figure 20:
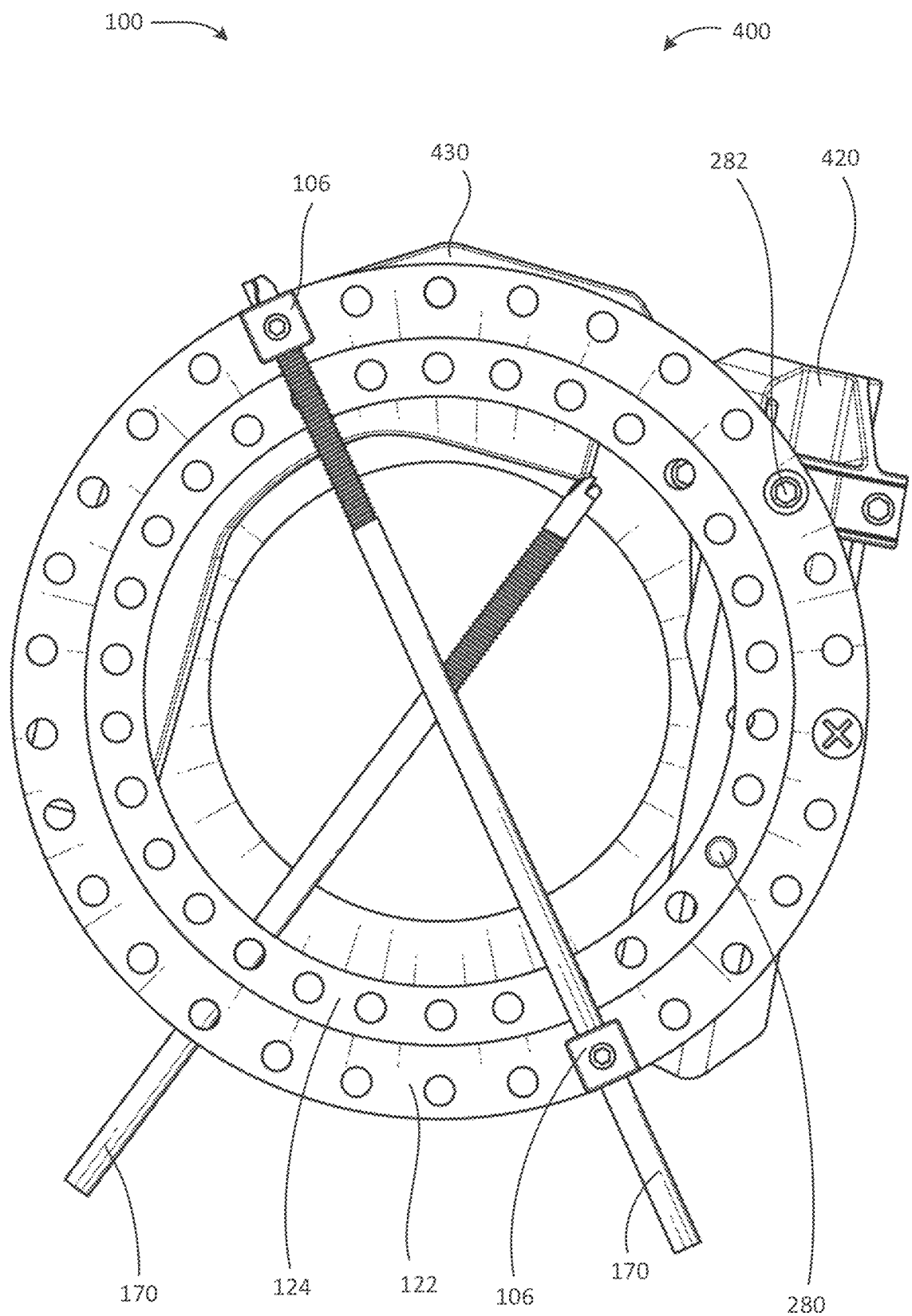
FIG. 20 is a bottom view of the coupled torsional fixator and stepper motor assembly of FIG. 16 at the first rotational position.
Figure 21:
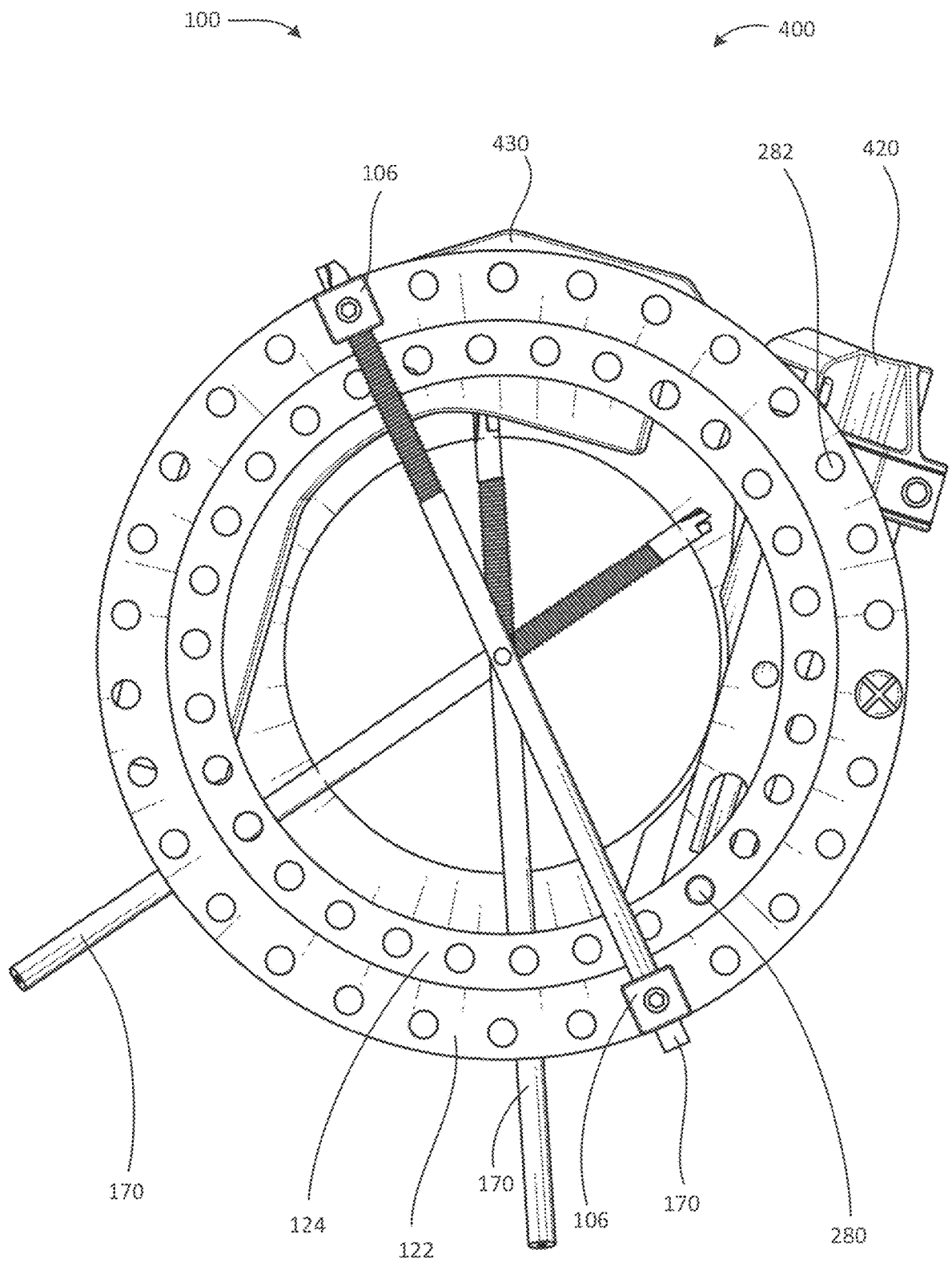
FIG. 21 is a bottom view of the coupled torsional fixator and stepper motor assembly of FIG. 16 at the second rotational position.

FIGS. 16-21 illustrate the coupled torsional fixator 100 of FIGS. 2-5 coupled with an automated control mechanism 400 comprising a stepper motor 420 that is electrically coupled to a battery 430 power source 410, according to an embodiment of the present disclosure. Specifically, FIG. 16 shows a top perspective view of the coupled torsional fixator 100 and stepper motor 420 assembly at a first rotational position; FIG. 17 shows another top perspective view of the coupled torsional fixator 100 and stepper motor 420 assembly at a second rotational position;

FIG. 18 shows a top view of the coupled torsional fixator 100 and stepper motor 420 assembly at the first rotational position; FIG. 19 shows another top view of the coupled torsional fixator 100 and stepper motor 420 assembly at the second rotational position; FIG. 20 shows a bottom view of the coupled torsional fixator 100 and stepper motor 420 assembly at the first rotational position; and FIG. 21 shows another bottom view of the coupled torsional fixator 100 and stepper motor 420 assembly at the second rotational position.

In some embodiments, the stepper motor 420 may be configured to receive power from an electronic power source (e.g., a battery, an external power source, etc.), rotate the first frame member to a desired relative rotational position with respect to the second frame member via power received from the electronic power source, and position the first bone fixation member at a desired second angle relative to the second bone fixation member to exert torsional force on the intact bone between the distal segment and the proximal segment, thereby externally reducing anteversion/retroversion of the intact bone.

In some embodiments, the stepper motor 420 may be coupled to a worm drive shaft or threaded drive shaft 440 to control rotation of the threaded drive shaft 440 in a step-wise fashion. The threaded drive shaft 440 may be configured to engage internal threading that is formed within the first fixation element 280 or the first fixation element head 220 to translate the first fixation element 280 along the threaded drive shaft 440 as it rotates to increase (and/or decrease) the effective length 405 of the automated control mechanism during the anteversion/retroversion treatment procedure.

In some embodiments, the threaded drive shaft 440 may be couplable with at least one of the first frame member and the second frame member, and the threaded drive shaft 440 may be configured to rotate the first frame member to a desired relative rotational position with respect to the second frame member.

In some embodiments, the threaded drive shaft 440 may be configured to couple with at least one of the first frame member and the second frame member via one of the fixation members, couplers, or fixation elements, (280, 282, 172, 180, 172) and/or any other suitable coupling device, which may be positioned intermediate the threaded drive shaft 440 and the first frame member or the second frame member to pivotally couple the threaded drive shaft 440 therewith.

In some embodiments, the rotational step movement of the stepper motor 420 may be controlled to achieve a predetermined translation amount for the first fixation element 280 along the threaded drive shaft 440 that corresponds to a desired rotational angle to be provided and maintained to an intact bone during the anteversion/retroversion treatment procedure.

In some embodiments, a set number of rotational step movements of the stepper motor 420 may correspond to a corresponding desired anteversion/retroversion treatment angle.

In some embodiments, the stepper motor 420 may be configured to apply and maintain one or more discrete torsional forces on the intact bone between the distal segment and the proximal segment.

In some embodiments, the rotational step movement of the stepper motor 420 may be controlled by a processor 450 that may be associated with the stepper motor 420 and/or in electronic communication with the stepper motor 420. The processor 450 may be programmed to control the rotational step movement of the stepper motor 420 over any period of time. For example, the processor may be programmed to actuate the stepper motor 420 to apply a set amount of anteversion/retroversion correction (e.g., 0.25 degrees, 0.5 degrees, 1 degree, more than 1 degree, etc.) over any regular or non-regular time intervals (e.g., any period(s) of time that are less than a day, once every day, or any time period(s) that are more than a day, etc.). In this manner, the intact bone may slowly correct its morphology during an automated anteversion/retroversion treatment procedure while the patient remains mobile.

In some embodiments, processor 450 may be programmed to control at least one rotational step movement of the stepper motor 420 over at least one period of time.

In some embodiments, the processor 450 may be programmed to control the rotational step movement of the stepper motor 420 and apply a plurality of discrete torsional forces on the intact bone between the distal segment and the proximal segment over at least one period of time.

In some embodiments, the automated control mechanism 400, such as the stepper motor 420, may be configured to apply a continuous torsional force on the intact bone between the distal segment and the proximal segment of the intact bone.

In some embodiments, the automated control mechanism 400, such as the stepper motor 420, may be configured to apply one or more discrete torsional forces on the intact bone between the distal segment and the proximal segment of the intact bone.

In some embodiments, the stepper motor 420 may be replaced with an alternative actuation system, such as a hydraulic actuator, a piezoelectric actuator, a spring, and/or the like. Such actuation systems may be powered electrically, hydraulically, chemically, or with mechanically stored energy. In each case, mechanisms may be used to control the rate at which the rotation of the bone occurs. For example, a ratchet mechanism (for example, with angled teeth on the first outer ring element 120 that interface with corresponding angled teeth on the second outer ring element 122), may be used to discretize rotational motion and/or ensure that it occurs in only the desired direction.

A linear actuator with limited linear travel (such as a piezoelectric actuator, a hydraulic actuator, or the like) may then apply sufficient force to rotate a desired number of increments per day, and may then move back to its original position. A mechanical energy storage device such as a spring (for example, a torsional spring, linear spring, leaf spring, or the like) may have sufficient energy stored at the outset to complete the entire procedure. In the alternative, such a device may have a manual "winding" mechanism by which the patient or another person can restore energy storage after deployment. For example, a linear spring may be lengthened or compressed sufficiently to rotate the bone for three days, after which time it may need to be lengthened or compressed again by a user. Although such systems may need some manual intervention, they may retain the advantage of automated incremental rotation. The processor 450 may still initiate expansion when desired, for example, by triggering a release coupled to the spring.

Figure 22:
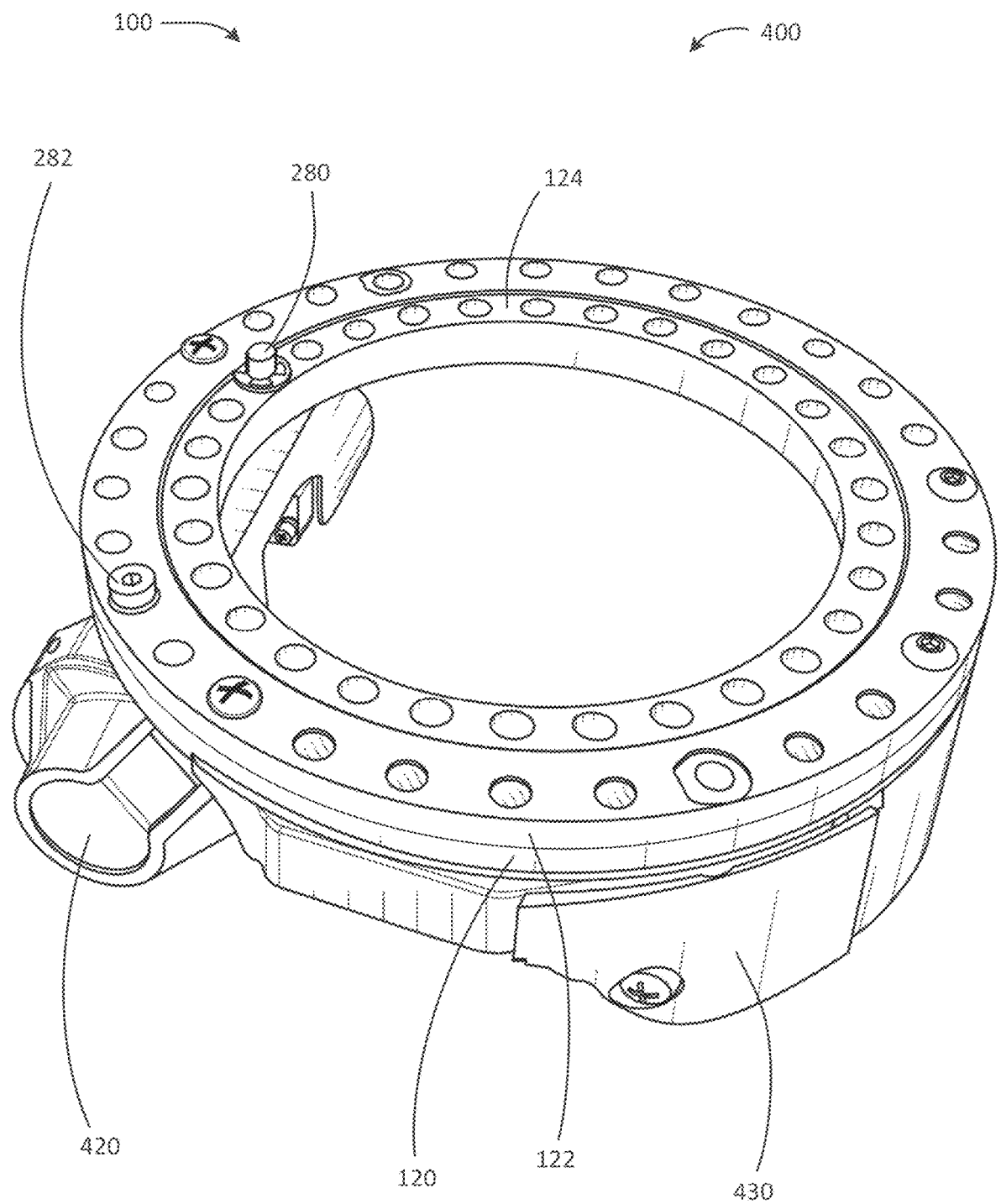
FIG. 22 is a bottom perspective view of the coupled torsional fixator and stepper motor assembly of FIG. 16 prior to fixation during a surgical procedure.
Figure 23:
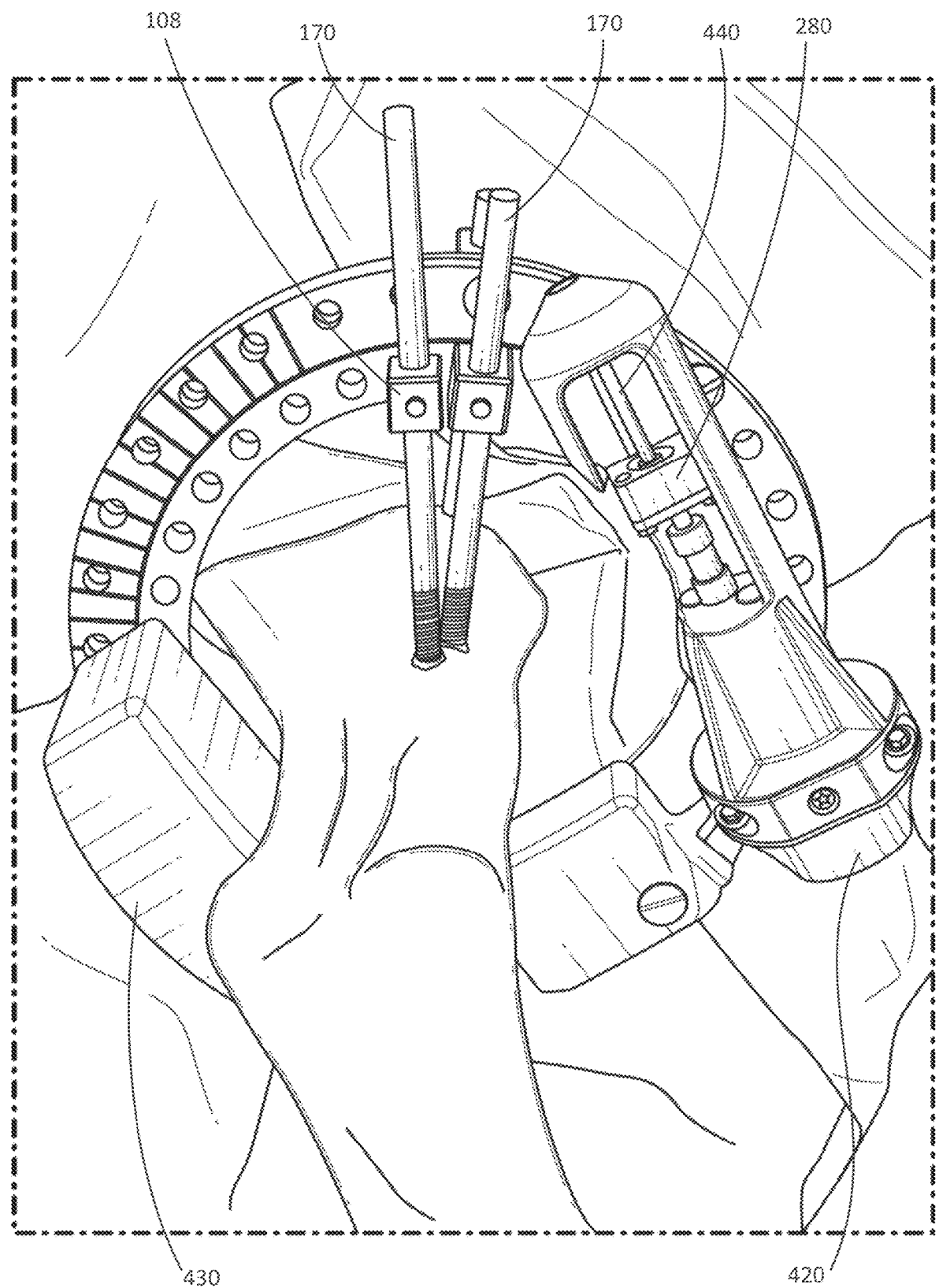
FIG. 23 is a bottom perspective view of the coupled torsional fixator and stepper motor assembly of FIG. 16 affixed to a femur bone of a sheep during the surgical procedure.
Figure 24:
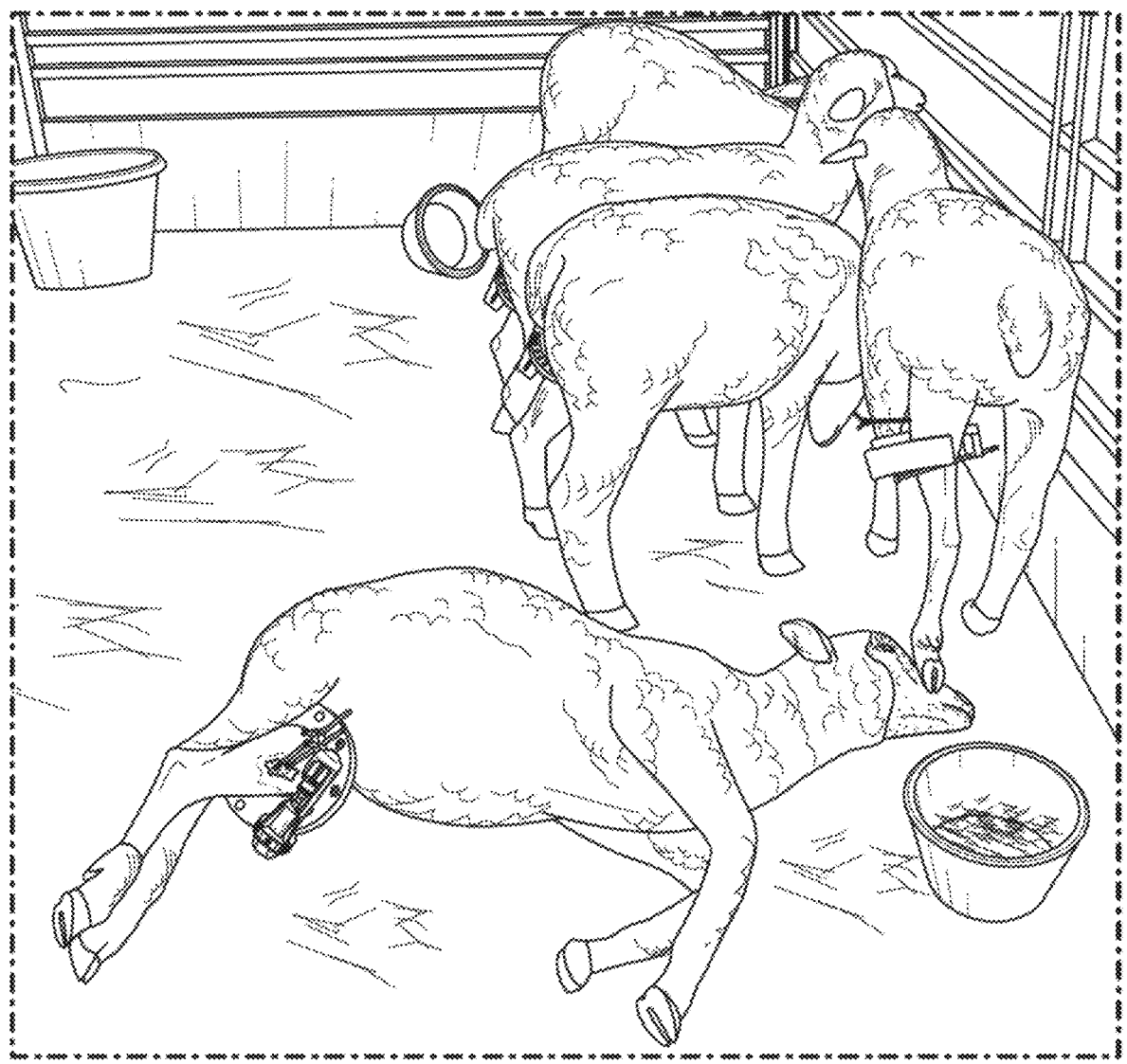
FIG. 24 shows multiple coupled torsional fixator and stepper motor assemblies affixed to femoral sheep bones.

FIGS. 22-24 illustrate various steps of an example fixation surgical procedure for the coupled torsional fixator and stepper motor assembly that is shown in FIGS. 16-21. Specifically, FIG. 22 is a bottom perspective view of the coupled torsional fixator and stepper motor assembly prior to fixation during a surgical procedure; FIG. 23 is a bottom perspective view of the coupled torsional fixator and stepper motor assembly of FIG. 22 being affixed to a femoral bone of a sheep; and FIG. 24 shows multiple coupled torsional fixator and stepper motor assemblies affixed to the femoral bones of sheep after the surgical procedure(s), with the sheep remaining mobile during the anteversion/retroversion treatment phase.

The steps of the fixation surgical procedure may be similar to those previously described herein, with the exception of the included automated control mechanism 400 (e.g., the stepper motor 420 for the embodiment shown in FIGS. 16-24). For example, if the amount of correction desired is 15°, the second fixation assembly 108 may be positioned to hold its pin 170 at a 15° angle relative to the first pin of the first fixation pin assembly 106. At this initial position, the pointer 168 (e.g., see FIG. 4) on the coupled ring assembly 102 may point at a location relative to the indicia 146 on the coupled ring assembly 102 to indicate an amount of anteversion/retroversion correction.

The coupled torsional fixator 100 can be gradually adjusted by actuation of the stepper motor 420 to gradually increase anteversion/retroversion correction over time. The stepper motor 420 may be rotated to adjust the length of the automated control mechanism 400 and thus rotate the inner ring element 124 (or second frame member, or second arcuate segment) relative to the outer ring assembly 103 (or first frame member, or first arcuate segment) to achieve a desired relative rotational position between the rotatably coupled first and second frame members. This will also adjust a distance/angle between the first and second fixation pin assemblies 106, 108 and their respective pins (e.g., from a first/initial angle to a second/desired angle). In doing so, the distal femur 8 will be gradually twisted relative to the femur shaft 4 to correct anteversion/retroversion.

In an embodiment of the method, the rate of anteversion/retroversion correction may be less than 1 degree per day or any other selected time period (e.g., 0.25 degrees per selected time period, 0.5 degrees per selected time period, etc.). In another embodiment of the method, the rate of anteversion/retroversion correction may be 1 degree per day or per selected time period. In yet another embodiment of the method, the rate may be more than 1 degree per day or per selected time period (e.g., 1.25 degrees per day or per selected time period, 1.5 degrees per day or per selected time period, etc.).

In some embodiments, the automated control mechanism 400 may be continuously actuated. For example, the automated control mechanism 400 may be configured to impart a set continuous amount of rotational force (or a selected range of rotational forces) to the intact bone independent of the angular position of the outer ring assembly 103 relative to the inner ring element 124. In this manner, the resistance of the intact bone during the morphological bone remodeling process may help determine the continuous amount of rotational force (or selected range of rotational forces) that is to be applied to the intact bone. In this manner, the rate of anteversion/retroversion correction implemented may vary depending on the resistance characteristics for a given intact bone throughout the morphological bone remodeling process during anteversion/retroversion correction.

In some embodiments of the method, the initial angle of the pins 170 relative to one another may vary, and the pins 170 need not be parallel to one another at the completion of the derotation process, or at any point during the derotation process. As anteversion/retroversion correction proceeds, the pins 170 may gradually move toward (or away from) one another until they reach a selected second angle, in at least some embodiments. In an embodiment, the selected second angle may be 0°, such that the pins 170 are vertically aligned from a superior or inferior perspective and they are parallel, or substantially parallel, relative to one another. At this juncture, the pointer 168 may be pointing at the zero degree indicator(s) of the indicia 146. After correction of the anteversion/retroversion, the torsional fixator 100 may be removed from the patient and the anteversion/retroversion correction procedure may end.

In some embodiments, a method for external anteversion/retroversion correction of an intact bone can utilize a device that may include: a first frame member and a second frame member rotatably coupled together, a first bone fixation member coupled to the first frame member, a second bone fixation member coupled to the second frame member, and an automated control mechanism 400 coupled to the first frame member and the second frame member.

In a first step of the method, the first bone fixation member may be percutaneously secured a distal segment of the intact bone, and the second bone fixation member may be percutaneously secured to a proximal segment of the intact bone at a first or initial angle relative to each other.

In a second step of the method, the automated control mechanism 400 may be activated to correct anteversion/retroversion of the intact bone via automation by: receiving power from a power source 410 in communication with the automated control mechanism 400, rotating the first frame member to a desired relative rotational position with respect to the second frame member via the power that is received from the power source 410 at the automated control mechanism 400, moving the second bone fixation member to a second or desired angle relative to the first bone fixation member, and applying a torsional force between the distal segment and the proximal segment to reduce anteversion/retroversion of the intact bone.

In some embodiments of the method, the power source 410 may include at least one of: a pressurized material, a mechanical spring, and a battery 430.

In some embodiments of the method, the automated control mechanism 400 may be configured to apply a continuous torsional force on the intact bone between the distal segment and the proximal segment.

In some embodiments of the method, the automated control mechanism 400 may be configured to apply one or more discrete torsional forces on the intact bone between the distal segment and the proximal segment.

In some embodiments of the method, the automated control mechanism 400 may include the stepper motor 420, and the power source 410 may include the battery 430 in electronic communication with the stepper motor 420.

In some embodiments of the method, the stepper motor 420 may be controlled by the processor 450 programmed to control at least one rotational step movement of the stepper motor 420 over at least one period of time.

The anteversion/retroversion correction systems and methods of the present disclosure may provide predictable rotational deformity correction, without the trauma and recovery time of an osteotomy. In some embodiments, the systems and methods may make it viable to correct rotational deformities that are debilitating for the patient, but not worth correcting due to the drawbacks of the osteotomy needed by a traditional method. For example, where a surgeon might only correct a rotational deformity exceeding 20° with traditional methods, the less invasive techniques presented herein may justify correcting less severe rotational deformities, for example, of 15°, 10°, or 5° or less.

Any procedures or methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112. It will be apparent to those having skill in the art that changes may be made to the details of the above-described embodiments without departing from the underlying principles set forth herein.

The phrases "connected to", "coupled to", "engaged with", and "in communication with" may refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, components that are removably and/or non-removably coupled with each other, components that are functionally coupled to each other through one or more intermediary components, etc. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of the present disclosure is not limited to the precise configurations and components disclosed herein. Various modifications, changes, and variations which will be apparent to those skilled in the art may be made in the arrangement, operation, and details of the devices, systems, and methods disclosed herein.

What is claimed is:

1. A system for external rotational deformity correction of an intact bone comprising:
    a first frame member;
    a second frame member rotatably coupled to the first frame member;
    a first bone fixation member coupled to the first frame member and extending therefrom to couple with a distal segment of the intact bone;
    a second bone fixation member coupled to the second frame member and extending therefrom to couple with a proximal segment of the intact bone at a first initial angle relative to the first bone fixation member;
    an automated control mechanism coupled to the first frame member and the second frame member; and
    a power source configured to provide power to the automated control mechanism,
    wherein the automated control mechanism is configured to:
        receive power from the power source;
        rotate the first frame member to a desired relative rotational position with respect to the second frame member; and
        position the first bone fixation member at a desired second angle relative to the second bone fixation member to exert torsional force on the intact bone between the distal segment and the proximal segment, and externally reduce rotational deformity of the intact bone.

2. The system of claim 1, wherein the power source comprises at least one of:
    a pressurized material;
    a mechanical spring; and
    a battery.

3. The system of claim 1, wherein the automated control mechanism is configured to apply a continuous torsional force on the intact bone between the distal segment and the proximal segment.

4. The system of claim 1, wherein the automated control mechanism is configured to apply one or more discrete torsional forces on the intact bone between the distal segment and the proximal segment.

5. The system of claim 1, wherein:
    the automated control mechanism comprises a stepper motor; and
    the power source comprises a battery in electronic communication with the stepper motor.

6. The system of claim 5, wherein the stepper motor is controlled by a processor programmed to control at least one rotational step movement of the stepper motor over at least one period of time.

7. The system of claim 6, wherein the processor is programmed to control the rotational step movement of the stepper motor and apply a plurality of discrete torsional forces on the intact bone between the distal segment and the proximal segment over the at least one period of time.

8. A system for external rotational deformity correction of an intact bone comprising:
    a first frame member;
    a second frame member rotatably coupled to the first frame member;
    a first bone fixation member coupled to the first frame member and extending therefrom to couple with a distal segment of the intact bone;
    a second bone fixation member coupled to the second frame member and extending therefrom to couple with a proximal segment of the intact bone at a first initial angle relative to the first bone fixation member; and
    a stepper motor coupled to the first frame member and the second frame member;
    wherein the stepper motor is configured to:
        receive power from an electronic power source;
        rotate the first frame member to a desired relative rotational position with respect to the second frame member via the power received from the electronic power source; and
        position the first bone fixation member at a desired second angle relative to the second bone fixation member to exert torsional force on the intact bone between the distal segment and the proximal segment, and externally reduce rotational deformity of the intact bone.

9. The system of claim 8, wherein:
    the stepper motor comprises a threaded drive shaft couplable with at least one of the first frame member and the second frame member; and
    the threaded drive shaft is configured to rotate the first frame member to the desired relative rotational position with respect to the second frame member.

10. The system of claim 9, wherein the threaded drive shaft is configured to couple with the at least one of the first frame member and the second frame member via a fixation member positioned intermediate the threaded drive shaft and the at least one of the first frame member and the second frame member.

11. The system of claim 8, wherein the electronic power source comprises a battery in electronic communication with the stepper motor.

12. The system of claim 8, wherein the stepper motor is configured to apply and maintain one or more discrete torsional forces on the intact bone between the distal segment and the proximal segment.

13. The system of claim 8, wherein the stepper motor is controlled by a processor programmed to control at least one rotational step movement of the stepper motor over at least one period of time.

14. The system of claim 13, wherein the processor is programmed to control the rotational step movement of the stepper motor to apply a plurality of discrete torsional forces on the intact bone between the distal segment and the proximal segment over the at least one period of time.

* * * * *